(12) United States Patent
Crine et al.

(10) Patent No.: US 7,763,712 B2
(45) Date of Patent: Jul. 27, 2010

(54) BONE DELIVERY CONJUGATES AND METHOD OF USING SAME TO TARGET PROTEINS TO BONE

(75) Inventors: Philippe Crine, Outremont (CA); Guy Boileau, Brossard (CA); Isabelle Lemire, Montréal (CA); Thomas P. Loisel, Montreéal (CA)

(73) Assignee: Enobia Pharma Inc., Montreal, Quebec (CA)

( * ) Notice: Subject to any disclaimer, the term of this patent is extended or adjusted under 35 U.S.C. 154(b) by 450 days.

(21) Appl. No.: 11/111,664

(22) Filed: Apr. 21, 2005

(65) Prior Publication Data

US 2006/0014687 A1 Jan. 19, 2006

Related U.S. Application Data

(60) Provisional application No. 60/563,828, filed on Apr. 21, 2004, provisional application No. 60/590,347, filed on Jul. 23, 2004, provisional application No. 60/614,984, filed on Oct. 4, 2004.

(51) Int. Cl.
*A61K 38/00* (2006.01)
*C07K 14/00* (2006.01)

(52) U.S. Cl. .......................................... 530/350; 514/2
(58) Field of Classification Search ........................ None
See application file for complete search history.

(56) References Cited

U.S. PATENT DOCUMENTS

| | | | |
|---|---|---|---|
| 6,290,952 B1 | 9/2001 | Poelstra et al. | |
| 6,420,384 B2 | 7/2002 | Weigele et al. | |
| 6,436,386 B1 | 8/2002 | Roberts et al. | |
| 6,455,495 B1 | 9/2002 | Orgel et al. | |
| 2004/0234518 A1* | 11/2004 | Crine et al. | 424/94.63 |
| 2005/0276796 A1 | 12/2005 | Tomatsu et al. | |
| 2007/0081984 A1 | 4/2007 | Tomatsu et al. | |
| 2007/0081986 A1 | 4/2007 | Tomatsu et al. | |

FOREIGN PATENT DOCUMENTS

| | | |
|---|---|---|
| JP | 8070875 B1 | 3/1996 |
| WO | WO 92/20371 A1 | 11/1992 |
| WO | WO 00/18954 A2 | 4/2000 |
| WO | WO 00/50580 A2 | 8/2000 |
| WO | WO 00/64486 A2 | 11/2000 |
| WO | WO 02/15918 A2 | 2/2002 |
| WO | WO 02/068579 A2 | 9/2002 |
| WO | 2006039480 A2 | 4/2006 |
| WO | 2008138131 A1 | 11/2008 |

OTHER PUBLICATIONS

Henthorn and Whyte, "Missense mutations of the Tissue-Nonspecific Alkaline Phosphatase gene in hypophosphatasia", Clin. Chem. 38/12, 2501-2505 (1992).*

Shull et al.,"Enzyme replacement in a canine model of Hurler syndrome", Proc. Natl. Acad. Sci. USA, vol. 91, pp. 12937-12941 (1994).*
Sharom and Lehto, "Glycosylphosphatidylinositol-anchored proteins: structure, function, and cleavage by phosphatidylinositol-specific phospholipase C", Biochem. Cell. Biol. 80: 535-549 (2002).*
Campbell et al., the American Physiological Society, 1997, vol. 273, pp. E1005-E1013.
Fujisaki et al., Journal of Drug Targeting, 1997, vol. 5, No. 2, pp. 129-138.
Fujisawa et al., Biochimica et Biophysica Acta 1292 (1996), pp. 53-60.
Gilbert et al., The Journal of Biological Chemistry, 2000, vol. 275, No. 21, pp. 16213-16218.
Hunter et al., Biochem J., (1994) 300, pp. 723-728.
Kasugai et al., Journal of Bone and Mineral Research, 2000, vol. 15, No. 5, pp. 936-943.
Patti et al., The Journal of Biological Chemistry, vol. 270, No. 20, pp. 12005-12011.
Rowe et al., Genomics. 2000, vol. 67, pp. 54-68.
Salih et al., The Journal of Biological Chemistry, 1997, vol. 272, No. 21, pp. 13966-13973.
Sekido et al., Journal of Drug Targeting, 2001, vol. 9, No. 2, pp. 111-121.
Symersky et al., Nature structural biology, 1997, vol. 4, No. 10, pp. 833-838.
Uludag et al., Biotechnol. Prog., 2000, vol. 16, pp. 1115-1118.
Weinberg, J., Clinical Therapeutics, 2003, vol. 25, No. 10, pp. 2487-2505.
Whyte et al., Journal of Bone and Mineral Research, 2003, vol. 18, No. 4, pp. 624-636.
Whyte, M.P., Endocrine Reviews, 1994, vol. 15, No. 4, pp. 439-461.
Whyte et al., The Journal of Pediatrics, 1982, vol. 101, No. 3, pp. 379-386.
Yokogawa et al., Endocrinology, 2001, vol. 142, No. 3, pp. 1228-1233.
Young et al., Clinical Orthopaedics and Related Research, 1992, No. 281, pp. 275-294.
Oda et al., J. Biochem, vol. 126: 694-699, (1999).
Kasugai et al., J Bone and Mineral Research, vol. 15: 936-943, (2000).
Bernardi et al. "Chromatography of Proteins on Hydroxyapatite." Methods in Enzymology, 1973, vol. XXVII: enzyme structure, Part D: 471-479.
Bobe et al. "Fas-Mediated Liver Damage in MRL Hemopoietic Chimeras Undergoing Ipr-mediated Graft-Versus-Host Disease." The Journal of Immunology, 1997, 159: 4197-4204.
Data sheet for pFUSE-SEAP-hFC, Invivogen, San Diego, CA.
Hosain et al. "Targeted Delivery of Antineoplastic Agent to Bone: Biodistribution Studies of Technetium-99m-Labeled Gem-Bisphosphonate Conjugate of Methotrexate." Journal of Nuclear Medicine,1996, 37:105-107.

(Continued)

*Primary Examiner*—Anand U Desai
(74) *Attorney, Agent, or Firm*—Clark & Elbing LLP

(57) ABSTRACT

A bone delivery conjugate having a structure selected from the group consisting of: A) X-$D_n$-Y-protein-Z; and B) Z-protein-Y-$D_n$-X, wherein X is absent or is an amino acid sequence of at least one amino acid; Y is absent or is an amino acid sequence of at least one amino acid; Z is absent or is an amino acid sequence of at least one amino acid; and $D_n$ is a poly aspartate wherein n=10 to 16. Compositions comprising same and methods of use thereof.

8 Claims, 18 Drawing Sheets

OTHER PUBLICATIONS

International Search Report for PCT/CA2008/000923 (Sep. 2008).

Kaufman et al. "Influence of Low Temperature on Production, Proteome, and Protein Phosphorylation of CHO cells." Biotechnol. Bioeng,1999, 63(5):573-582.

Nishioka et al. "Enhancement of Drug Delivery to Bone: Characterization of Human Tissue-Nonspecific Alkaline Phosphatase Tagged with an Acid Oligopeptide." Molecular Genetics and Metabolism, 2006, 88:244-255.

Office Actions mailed by the United States Patent and Trademark Office in connection with U.S. Appl. No. 11/484,870, filed on Jul. 11, 2006 and published as US 2007-0081984 A1.

Spears et al. "Deoxyuridate Effects on Thymidylate Synthase 5-Fluorodeoxyuridylate-Folate Ternary Complex Formation." Biochem. Pharmacol. 1989, 38(18):2985-2993.

Sturtz et al. "A Study of the Delivery-Targeting Concept Applied to Antineoplastic Drugs Active on Human Osteosarcoma I. Synthesis and Biological Activity in Nude Mice Carrying Human Osteosarcoma Xenografts of Gem-Bisphosphonic Methotrexate Analogues." European Journal of Medicinal Chemistry, Chimica Therapeutica, 1992. 27 (8):825-833.

Written Opinion for PCT/CA2008/000923 (Sep. 2008).

Patti et al., The Journal of Biological Chemistry, vol. 270, No. 20 pp. 12005-12011. (1995).

* cited by examiner

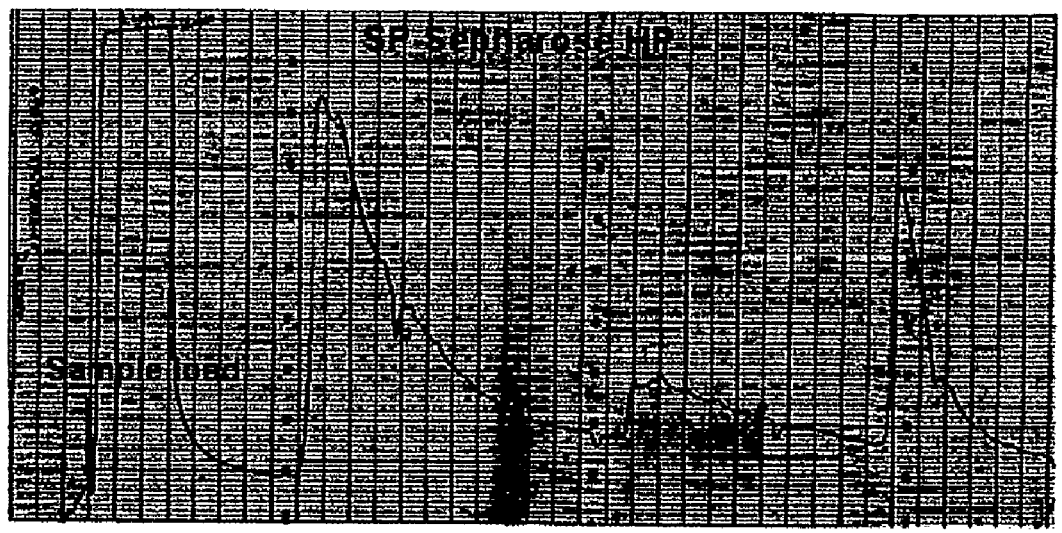
Figure 4

```
atggaagcagaaacagggagcagcgtggagactggaaagaaggccaacagaggcactcgaattgccctgg
tcgtgtttgtcctgacagtgatcgctcaacaaacaaccagtcaaggtctcttatccggagatgacgatga
cgatgacgatgacgatgactccggaagtctccaagctaaacaggagtactgcctgaagccagaatgcatc
gaagcggctgctgccatcttaagtaaagtaaatctgtctgtggatccttgtgataatttcttccggttcg
cttgtgatggctggataagcaataatccaattcccgaagatatgccaagctatggggtttatccttggct
gagacataatgttgacctcaagttgaaggaacttttggagaaatcaatcagtagaaggcgggacaccgaa
gccatacagaaagccaaaatcctttattcatcctgcatgaatgagaaagcgattgaaaaagcagatgcca
agccactgctacacatcctacggcattcacctttccgctggcccgtgcttgaatctaatattggccctga
aggggtttggtcagagagaaagttcagccttctgcagacacttgcaacgtttcgtggtcaatacagcaat
tctgtgttcatccgtttgtatgtgtcccctgatgacaaagcatccaatgaacatatcttgaagctggacc
aagcaacactctccctggccgtgagggaagactaccttgataacagtacagaagccaagtcttatcggga
tgcccttacaagttcatggtggatactgccgtgctttaggagctaacagttccagagcagagcatgac
atgaagtcagtgctcagattggaaattaagatagctgagataatgattccacatgaaaaccgaaccagcg
aggccatgtacaacaaaatgaacatttctgaactgagtgctatgattccccagttcgactggctgggcta
catcaagaaggtcattgacaccagactctaccccatctgaaagacatcagcccctccgagaatgtggtg
gtccgcgtcccgcagtactttaaagatttgtttaggatattagggtctgagagaaagaagaccattgcca
actatttggtgtggagaatggtttattccagaattccaaaccttagcaggcgctttcagtatagatggct
ggaattctcaagggtaatccaggggaccacaactttgctgcctcaatgggacaaatgtgtaaactttatt
gaaagtgccctcccttatgttgttggaaagatgtttgtagatgtgtacttccaggaagataagaaggaaa
tgatggaggaattggttgagggcgttcgctgggcctttattgacatgctagagaaagaaaatgagtggat
ggatgcaggaacgaaaaggaaagccaaagaaaaggcgagagctgttttggcaaaagttggctatccagag
tttataatgaatgatactcatgttaatgaagacctcaaagctatcaagttttcagaagccgactactttg
gcaacgtcctacaaactcgcaagtatttagcacagtctgatttcttctggctaagaaaagccgttccaaa
aacagagtggtttacaaatccgacgactgtcaatgccttctacagtgcatccaccaaccagatccgattt
ccagcaggagagctccagaagcctttcttttggggaacagaatatcctcgatctctgagttatggtgcta
taggagtaattgtcggacatgaatttacacatggatttgataataatggtagaaaatatgataaaaatgg
aaacctggatccttggtggtctactgaatcagaagaaaagtttaaggaaaaaacaaaatgcatgattaac
cagtatagcaactattattggaagaaagctggcttaaatgtcaaggggaagaggaccctgggagaaaata
ttgctgataatggaggcctgcgggaagcttttagggcttacaggaaatggataaatgacagaaggcaggg
acttgaggagcctcttctaccaggcatcacattcaccaacaaccagctcttcttcctgagttatgctcat
gtgaggtgcaattcctacagaccagaagctgcccgagaacaagtccaaattggtgctcacagtcccctc
agtttagggtcaatggtgcaattagtaactttgaagaattccagaaagcttttaactgtccacccaattc
cacgatgaacagaggcatggactcctgccgactctggtag
```

Figure 7

```
MEAETGSSVETGKKANRGTRIALVVFVLTVIAQQTTSQGLLSGDDDDDDDDDSGSLQAKQEYCLKPECI
EAAAAILSKVNLSVDPCDNFFRFACDGWISNNPIPEDMPSYGVYPWLRHNVDLKLKELLEKSISRRRDTE
AIQKAKILYSSCMNEKAIEKADAKPLLHILRHSPFRWPVLESNIGPEGVWSERKFSLLQTLATFRGQYSN
SVFIRLYVSPDDKASNEHILKLDQATLSLAVREDYLDNSTEAKSYRDALYKFMVDTAVLLGANSSRAEHD
MKSVLRLEIKIAEIMIPHENRTSEAMYNKMNISELSAMIPQFDWLGYIKKVIDTRLYPHLKDISPSENVV
VRVPQYFKDLFRILGSERKKTIANYLVWRMVYSRIPNLSRRFQYRWLEFSRVIQGTTTLLPQWDKCVNFI
ESALPYVVGKMFVDVYFQEDKKEMMEELVEGVRWAFIDMLEKENEWMDAGTKRKAKEKARAVLAKVGYPE
FIMNDTHVNEDLKAIKFSEADYFGNVLQTRKYLAQSDFFWLRKAVPKTEWFTNPTTVNAFYSASTNQIRF
PAGELQKPFFWGTEYPRSLSYGAIGVIVGHEFTHGFDNNGRKYDKNGNLDPWWSTESEEKFKEKTKCMIN
QYSNYYWKKAGLNVKGKRTLGENIADNGGLREAFRAYRKWINDRRQGLEEPLLPGITFTNNQLFFLSYAH
VRCNSYRPEAAREQVQIGAHSPPQFRVNGAISNFEEFQKAFNCPPNSTMNRGMDSCRLW
```

Figure 8

```
  1 MEAETGSSVE TGKKANRGTR IALVVFVGGT LVLGTILFLV SQGLLSLQAK QEYCLKPECI
 61 EAAAAILSKV NLSVDPCDNF FRFACDGWIS NNPIPEDMPS YGVYPWLRHN VDLKLKELLE
121 KSISRRRDTE AIQKAKILYS SCMNEKAIEK ADAKPLLHIL RHSPFRWPVL ESNIGPEGVW
181 SERKFSLLQT LATFRGQYSN SVFIRLYVSP DDKASNEHIL KLDQATLSLA VREDYLDNST
241 EAKSYRDALY KFMVDTAVLL GANSSRAEHD MKSVLRLEIK IAEIMIPHEN RTSEAMYNKM
301 NISELSAMIP QFDWLGYIKK VIDTRLYPHL KDISPSENVV VRVPQYFKDL FRILGSERKK
361 TIANYLVWRM VYSRIPNLSR RFQYRWLEFS RVIQGTTTLL PQWDKCVNFI ESALPYVVGK
421 MFVDVYFQED KKEMMEELVE GVRWAFIDML EKENEWMDAG TKRKAKEKAR AVLAKVGYPE
481 FIMNDTHVNE DLKAIKFSEA DYFGNVLQTR KYLAQSDFFW LRKAVPKTEW FTNPTTVNAF
541 YSASTNQIRF PAGELQKPFF WGTEYPRSLS YGAIGVIVGH EFTHGFDNNG RKYDKNGNLD
601 PWWSTESEEK FKEKTKCMIN QYSNYYWKKA GLNVKGKRTL GENIADNGGL REAFRAYRKW
661 INDRRQGLEE PLLPGITFTN NQLFFLSYAH VRCNSYRPEA AREQVQIGAH SPPQFRVNGA
721 ISNSEEFQKA FNCPPNSTMN RGMDSCRLW
```

Figure 10

SGDDDDDDDDDDSGSLQAKQEYCLKPECIEAAAAILSKVNLSVDPCDNFFRFACDGWISNNPIPEDMPSY
GVYPWLRHNVDLKLKELLEKSISRRRDTEAIQKAKILYSSCMNEKAIEKADAKPLLHILRHSPFRWPVLE
SNIGPEGVWSERKFSLLQTLATFRGQYSNSVFIRLYVSPDDKASNEHILKLDQATLSLAVREDYLDNSTE
AKSYRDALYKFMVDTAVLLGANSSRAEHDMKSVLRLEIKIAEIMIPHENRTSEAMYNKMNISELSAMIPQ
FDWLGYIKKVIDTRLYPHLKDISPSENVVVRVPQYFKDLFRILGSERKKTIANYLVWRMVYSRIPNLSRR
FQYRWLEFSRVIQGTTTLLPQWDKCVNFIESALPYVVGKMFVDVYFQEDKKEMMEELVEGVRWAFIDMLE
KENEWMDAGTKRKAKEKARAVLAKVGYPEFIMNDTHVNEDLKAIKFSEADYFGNVLQTRKYLAQSDFFWL
RKAVPKTEWFTNPTTVNAFYSASTNQIRFPAGELQKPFFWGTEYPRSLSYGAIGVIVGHEFTHGFDNNGR
KYDKNGNLDPWWSTESEEKFKEKTKCMINQYSNYYWKKAGLNVKGKRTLGENIADNGGLREAFRAYRKWI
NDRRQGLEEPLLPGITFTNNQLFFLSYAHVRCNSYRPEAAREQVQIGAHSPPQFRVNGAISNFEEFQKAF
NCPPNSTMNRGMDSCRLW

Figure 11

| Protein construct | Specific activity (UA*/sec/μg) | Schematic representation |
|---|---|---|
| 1 | sPHEX | 10.3 | SLQAK...(SEQ ID NO: 45) |
| 2 | FC-sPHEX | 5.75 | TSDKTH...SLQAK...(SEQ ID NO: 46) |
| 3 | pCDNA3-2SV-NL1furin-sPHEX | N/A | SVSLQAK...(SEQ ID NO: 47) |
| 4 | D$_{10}$sPHEX | 12.0 | (GDDDDDDDDD)SGSLQAK...(SEQ ID NO: 48) |
| 5 | D$_{10}$sPHEX | 8.55 | (GDDDDDDDDD)YVSLQAK...(SEQ ID NO: 49) |

▨ : Represents the mutated transmembrane domain of PHEX.

■ : Represents the human IgG1 signal peptide.

▩ : Represents the human IgG1 heavy chain domains hinge, CH2 and CH3.

□ : N-terminal sequence with the furin cleavage site (RTVVKR(SV))(SEQ ID NO: 50)

▤ : Furin cleavage site.

— : peptidase signal cleavage site

```
        BamHI
        ~~~~~~
   1    GGATCCACCA TGATTTCACC ATTCTTAGTA CTGGCCATTG GCACCTGCCT TACTAACTCC TTAGTGCCAG
  71    AGAAAGAGAA AGACCCCAAG TACTGGCGAG ACCAAGCGCA AGAGACACTG AAATATGCCC TGGAGCTTCA
 141    GAAGCTCAAC ACCAACGTGG CTAAGAATGT CATCATGTTC CTGGGAGATG GGATGGGTGT CTCCACAGTG
 211    ACGGCTGCCC GCATCCTCAA GGGTCAGCTC CACCACAACC CTGGGGAGGA GACCAGGCTG GAGATGGACA
 281    AGTTCCCCTT CGTGGCCCTC TCCAAGACGT ACAACACCAA TGCCCAGGTC CCTGACAGCG CCGGCACCGC
 351    CACCGCCTAC CTGTGTGGGG TGAAGGCCAA TGAGGGCACC GTGGGGGTAA GCGCAGCCAC TGAGCGTTCC
 421    CGGTGCAACA CCACCCAGGG GAACGAGGTC ACCTCCATCC TGCGCTGGGC CAAGGACGCT GGGAAATCTG
 491    TGGGCATTGT GACCACCACG AGAGTGAACC ATGCCACCCC CAGCGCCGCC TACGCCCACT CGGCTGACCG
 561    GGACTGGTAC TCAGACAACG AGATGCCCCC TGAGGCCTTG AGCCAGGGCT GTAAGGACAT CGCCTACCAG
 631    CTCATGCATA ACATCAGGGA CATTGACGTG ATCATGGGGG GTGGCCGGAA ATACATGTAC CCCAAGAATA
 701    AAACTGATGT GGAGTATGAG AGTGACGAGA AGCCAGGGG CACGAGGCTG GACGGCCTGG ACCTCGTTGA
 771    CACCTGGAAG AGCTTCAAAC CGAGATACAA GCACTCCCAC TTCATCTGGA ACCGCACGGA ACTCCTGACC
 841    CTTGACCCCC ACAATGTGGA CTACCTATTG GGTCTCTTCG AGCCAGGGGA CATGCAGTAC GAGCTGAACA
 911    GGAACAACGT GACGGACCCG TCACTCTCCG AGATGGTGGT GGTGGCCATC CAGATCCTGC GGAAGAACCC
 981    CAAAGGCTTC TTCTTGCTGG TGGAAGGAGG CAGAATTGAC CACGGGCACC ATGAAGGAAA AGCCAAGCAG
1051    GCCCTGCATG AGGCGGTGGA GATGGACCGG GCCATCGGGC AGGCAGGCAG CTTGACCTCC TCGGAAGACA
1121    CTCTGACCGT GGTCACTGCG GACCATTCCC ACGTCTTCAC ATTTGGTGGA TACACCCCCC GTGGCAACTC
1191    TATCTTTGGT CTGGCCCCCA TGCTGAGTGA CACAGACAAG AAGCCCTTCA CTGCCATCCT GTATGGCAAT
1261    GGGCCTGGCT ACAAGGTGGT GGGCGGTGAA CGAGAGAATG TCTCCATGGT GGACTATGCT CACAACAACT
1331    ACCAGGCGCA GTCTGCTGTG CCCCTGCGCC ACGAGACCCA CGGCGGGGAG GACGTGGCCG TCTTCTCCAA
1401    GGGCCCCATG GCGCACCTGC TGCACGGCGT CCACGAGCAG AACTACGTCC CCACGTGAT GGCGTATGCA
                                                                           XbaI
                                                                           ~~~~~~~
1471    GCCTGCATCG GGGCCAACCT CGGCCACTGT GCTCCTGCCA GCTCGTAGTC TAGA
```

B

```
   1    MISPFLVLAI GTCLTNSLVP EKEKDPKYWR DQAQETLKYA LELQKLNTNV
  51    AKNVIMFLGD GMGVSTVTAA RILKGQLHHN PGEETRLEMD KFPFVALSKT
 101    YNTNAQVPDS AGTATAYLCG VKANEGTVGV SAATERSRCN TTQGNEVTSI
 151    LRWAKDAGKS VGIVTTTRVN HATPSAAYAH SADRDWYSDN EMPPEALSQG
 201    CKDIAYQLMH NIRDIDVIMG GGRKYMYPKN KTDVEYESDE KARGTRLDGL
 251    DLVDTWKSFK PRYKHSHFIW NRTELLTLDP HNVDYLLGLF EPGDMQYELN
 301    RNNVTDPSLS EMVVVAIQIL RKNPKGFFLL VEGGRIDHGH HEGKAKQALH
 351    EAVEMDRAIG QAGSLTSSED TLTVVTADHS HVFTFGGYTP RGNSIFGLAP
 401    MLSDTDKKPF TAILYGNGPG YKVVGGEREN VSMVDYAHNN YQAQSAVPLR
 451    HETHGGEDVA VFSKGPMAHL LHGVHEQNYV PHVMAYAACI GANLGHCAPA
 501    SS
```

```
          BamHI
          ~~~~~~
    1     GGATCCACCA TGATTTCACC ATTCTTAGTA CTGGCCATTG GCACCTGCCT TACTAACTCC TTAGTGCCAG
   71     AGAAAGAGAA AGACCCCAAG TACTGGCGAG ACCAAGCGCA AGAGACACTG AAATATGCCC TGGAGCTTCA
  141     GAAGCTCAAC ACCAACGTGG CTAAGAATGT CATCATGTTC CTGGGAGATG GGATGGGTGT CTCCACAGTG
  211     ACGGCTGCCC GCATCCTCAA GGGTCAGCTC CACCACAACC CTGGGGAGGA GACCAGGCTG AGATGGACA
  281     AGTTCCCCTT CGTGGCCCTC TCCAAGACGT ACAACACCAA TGCCCAGGTC CCTGACAGCG CCGGCACCGC
  351     CACCGCCTAC CTGTGTGGGG TGAAGGCCAA TGAGGGCACC GTGGGGGTAA GCGCAGCCAC TGAGCGTTCC
  421     CGGTGCAACA CCACCCAGGG AACGAGGTC ACCTCCATCC TGCGCTGGGC CAAGGACGCT GGGAAATCTG
  491     TGGGCATTGT GACCACCACG AGAGTGAACC ATGCCACCCC CAGCGCCGCC TACGCCCACT CGGCTGACCG
  561     GGACTGGTAC TCAGACAACG AGATGCCCCC TGAGGCCTTG AGCCAGGGCT GTAAGGACAT CGCCTACCAG
  631     CTCATGCATA ACATCAGGGA CATTGACGTG ATCATGGGGG GTGGCCGGAA ATACATGTAC CCCAAGAATA
  701     AAACTGATGT GGAGTATGAG AGTGACGAGA AAGCCAGGGG CACGAGGCTG GACGGCCTGG ACCTCGTTGA
  771     CACCTGGAAG AGCTTCAAAC CGAGATACAA GCACTCCCAC TTCATCTGGA ACCGCACGGA ACTCCTGACC
  841     CTTGACCCCC ACAATGTGGA CTACCTATTG GGTCTCTTCG AGCCAGGGGA CATGCAGTAC GAGCTGAACA
  911     GGAACAACGT GACGGACCCG TCACTCTCCG AGATGGTGGT GGTGGCCATC CAGATCCTGC GGAAGAACCC
  981     CAAAGGCTTC TTCTTGCTGG TGGAAGGAGG CAGAATTGAC CACGGGCACC ATGAAGGAAA AGCCAAGCAG
 1051     GCCCTGCATG AGGCGGTGGA GATGGACCGG GCCATCGGGC AGGCAGGCAG CTTGACCTCC TCGGAAGACA
 1121     CTCTGACCGT GGTCACTGCG GACCATTCCC ACGTCTTCAC ATTTGGTGGA TACACCCCCC GTGGCAACTC
 1191     TATCTTTGGT CTGGCCCCCA TGCTGAGTGA CACAGACAAG AAGCCCTTCA CTGCCATCCT GTATGGCAAT
 1261     GGGCCTGGCT ACAAGGTGGT GGGCGGTGAA CGAGAGAATG TCTCCATGGT GGACTATGCT CACAACAACT
 1331     ACCAGGCGCA GTCTGCTGTG CCCCTGCGCC ACGAGACCCA CGGCGGGGAG GACGTGGCCG TCTTCTCCAA
 1401     GGGCCCCATG GCGCACCTGC TGCACGGCGT CCACGAGCAG AACTACGTCC CCACGTGAT GGCGTATGCA
 1471     GCCTGCATCG GGGCCAACCT CGGCCACTGT GCTCCTGCCA GCTCGGATGA CGACGATGAT GACGATGATG
                 XbaI
                 ~~~~~~
 1541     ACGACTAGTC TAGA
```

B

```
    1     MISPFLVLAI GTCLTNSLVP EKEKDPKYWR DQAQETLKYA LELQKLNTNV
   51     AKNVIMFLGD GMGVSTVTAA RILKGQLHHN PGEETRLEMD KFPFVALSKT
  101     YNTNAQVPDS AGTATAYLCG VKANEGTVGV SAATERSRCN TTQGNEVTSI
  151     LRWAKDAGKS VGIVTTTRVN HATPSAAYAH SADRDWYSDN EMPPEALSQG
  201     CKDIAYQLMH NIRDIDVIMG GRKYMYPKN KTDVEYESDE KARGTRLDGL
  251     DLVDTWKSFK PRYKHSHFIW NRTELLTLDP HNVDYLLGLF EPGDMQYELN
  301     RNNVTDPSLS EMVVVAIQIL RKNPKGFFLL VEGGRIDHGH HEGKAKQALH
  351     EAVEMDRAIG QAGSLTSSED TLTVVTADHS HVFTFGGYTP RGNSIFGLAP
  401     MLSDTDKKPF TAILYGNGPG YKVVGGEREN VSMVDYAHNN YQAQSAVPLR
  451     HETHGGEDVA VFSKGPMAHL LHGVHEQNYV PHVMAYAACI GANLGHCAPA
  501     SSDDDDDDDD DD
```

Figure 17

SEQUENCE LISTING

<160> NUMBER OF SEQ ID NOS: 50

<210> SEQ ID NO 1
<211> LENGTH: 2280
<212> TYPE: DNA
<213> ORGANISM: Artificial Sequence
<220> FEATURE:
<223> OTHER INFORMATION: Encoding cleavable conjugate

<400> SEQUENCE: 1

```
atggaagcag aaacagggag cagcgtggag actggaaaga aggccaacag aggcactcga      60
attgccctgg tcgtgtttgt cctgacagtg atcgctcaac aaacaaccag tcaaggtctc     120
ttatccggag atgacgatga cgatgacgat gacgatgact ccggaagtct ccaagctaaa     180
caggagtact gcctgaagcc agaatgcatc gaagcggctg ctgccatctt aagtaaagta     240
aatctgtctg tggatccttg tgataatttc ttccggttcg cttgtgatgg ctggataagc     300
aataatccaa ttcccgaaga tatgccaagc tatgggggttt atccttggct gagacataat     360
gttgacctca gttgaagga acttttggag aaatcaatca gtagaaggcg ggacaccgaa     420
gccatacaga aagccaaaat cctttattca tcctgcatga atgagaaagc gattgaaaaa     480
gcagatgcca agccactgct acacatccta cggcattcac ctttccgctg gcccgtgctt     540
gaatctaata ttggccctga aggggtttgg tcagagagaa agttcagcct tctgcagaca     600
cttgcaacgt ttcgtggtca atacagcaat tctgtgttca tccgtttgta tgtgtcccct     660
gatgacaaag catccaatga acatatcttg aagctggacc aagcaacact ctccctggcc     720
gtgagggaag actaccttga taacagtaca gaagccaagt cttatcggga tgcccttac     780 aagttcatgg tggatactgc cgtgcttta ggagctaaca gttccagagc agagcatgac     840
atgaagtcag tgctcagatt ggaaattaag atagctgaga taatgattcc acatgaaaac     900
cgaaccagcg aggccatgta caacaaaatg aacatttctg aactgagtgc tatgattccc     960
cagttcgact ggctgggcta catcaagaag gtcattgaca ccagactcta cccccatctg    1020
aaagacatca gcccctccga gaatgtggtg gtccgcgtcc cgcagtactt taaagatttg    1080
tttaggatat tagggtctga gagaagaag accattgcca actatttggt gtggagaatg    1140
gtttattcca gaattccaaa ccttagcagg cgctttcagt atagatggct ggaattctca    1200
agggtaatcc aggggaccac aactttgctg cctcaatggg acaaatgtgt aaactttatt    1260
gaaagtgccc tcccttatgt tgttggaaag atgtttgtag atgtgtactt ccaggaagat    1320
```

```
aagaaggaaa tgatggagga attggttgag ggcgttcgct gggccttat tgacatgcta    1380 gagaaagaaa atgagtggat ggatgcagga acgaaaagga aagccaaaga aaggcgaga    1440 gctgttttgg caaaagttgg ctatccagag tttataatga atgatactca tgttaatgaa    1500
gacctcaaag ctatcaagtt ttcagaagcc gactactttg caacgtcct acaaactcgc    1560 aagtatttag cacagtctga tttcttctgg ctaagaaaag ccgttccaaa aacagagtgg    1620
tttacaaatc cgacgactgt caatgccttc tacagtgcat ccaccaacca gatccgattt    1680
ccagcaggag agctccagaa gccttctttt tggggaacag aatatcctcg atctctgagt    1740
tatggtgcta taggagtaat tgtcggacat gaatttacac atggatttga taataatggt    1800
agaaaatatg ataaaaatgg aaacctggat ccttggtggt ctactgaatc agaagaaaag    1860
tttaaggaaa aacaaaatg catgattaac cagtatagca actattattg gaagaaagct    1920
ggcttaaatg tcaaggggaa gaggaccctg ggagaaaata ttgctgataa tggaggcctg    1980
cgggaagctt ttagggctta caggaaatgg ataaatgaca gaaggcaggg acttgaggag    2040
cctcttctac caggcatcac attcaccaac aaccagctct tcttcctgag ttatgctcat    2100
gtgaggtgca attcctacag accagaagct gcccgagaac aagtccaaat tggtgctcac    2160 agtcccctc agtttagggt caatggtgca attagtaact ttgaagaatt ccagaaagct    2220
tttaactgtc cacccaattc cacgatgaac agaggcatgg actcctgccg actctggtag    2280

<210> SEQ ID NO 2
<211> LENGTH: 759
<212> TYPE: PRT
<213> ORGANISM: Artificial Sequence
<220> FEATURE:
<223> OTHER INFORMATION: Cleavable PHEX conjugate

<400> SEQUENCE: 2

Met Glu Ala Glu Thr Gly Ser Ser Val Glu Thr Gly Lys Lys Ala Asn
1               5                   10                  15

Arg Gly Thr Arg Ile Ala Leu Val Val Phe Val Leu Thr Val Ile Ala
                20                  25                  30

Gln Gln Thr Thr Ser Gln Gly Leu Leu Ser Gly Asp Asp Asp Asp
            35                  40                  45

Asp Asp Asp Asp Asp Ser Gly Ser Leu Gln Ala Lys Gln Glu Tyr Cys
    50                  55                  60

Leu Lys Pro Glu Cys Ile Glu Ala Ala Ala Ile Leu Ser Lys Val
65                  70                  75                  80

Asn Leu Ser Val Asp Pro Cys Asp Asn Phe Phe Arg Phe Ala Cys Asp
                85                  90                  95

Gly Trp Ile Ser Asn Asn Pro Ile Pro Glu Asp Met Pro Ser Tyr Gly
            100                 105                 110

Val Tyr Pro Trp Leu Arg His Asn Val Asp Leu Lys Leu Lys Glu Leu
        115                 120                 125

Leu Glu Lys Ser Ile Ser Arg Arg Arg Asp Thr Glu Ala Ile Gln Lys
    130                 135                 140

Ala Lys Ile Leu Tyr Ser Ser Cys Met Asn Glu Lys Ala Ile Glu Lys
145                 150                 155                 160

Ala Asp Ala Lys Pro Leu Leu His Ile Leu Arg His Ser Pro Phe Arg
                165                 170                 175

Trp Pro Val Leu Glu Ser Asn Ile Gly Pro Glu Gly Val Trp Ser Glu
            180                 185                 190

Arg Lys Phe Ser Leu Leu Gln Thr Leu Ala Thr Phe Arg Gly Gln Tyr
```

-continued

```
            195                 200                 205
Ser Asn Ser Val Phe Ile Arg Leu Tyr Val Ser Pro Asp Asp Lys Ala
    210                 215                 220

Ser Asn Glu His Ile Leu Lys Leu Asp Gln Ala Thr Leu Ser Leu Ala
225                 230                 235                 240

Val Arg Glu Asp Tyr Leu Asp Asn Ser Thr Glu Ala Lys Ser Tyr Arg
                245                 250                 255

Asp Ala Leu Tyr Lys Phe Met Val Asp Thr Ala Val Leu Leu Gly Ala
                260                 265                 270

Asn Ser Ser Arg Ala Glu His Asp Met Lys Ser Val Leu Arg Leu Glu
            275                 280                 285

Ile Lys Ile Ala Glu Ile Met Ile Pro His Glu Asn Arg Thr Ser Glu
    290                 295                 300

Ala Met Tyr Asn Lys Met Asn Ile Ser Glu Leu Ser Ala Met Ile Pro
305                 310                 315                 320

Gln Phe Asp Trp Leu Gly Tyr Ile Lys Lys Val Ile Asp Thr Arg Leu
                325                 330                 335

Tyr Pro His Leu Lys Asp Ile Ser Pro Ser Glu Asn Val Val Val Arg
                340                 345                 350

Val Pro Gln Tyr Phe Lys Asp Leu Phe Arg Ile Leu Gly Ser Glu Arg
            355                 360                 365

Lys Lys Thr Ile Ala Asn Tyr Leu Val Trp Arg Met Val Tyr Ser Arg
    370                 375                 380

Ile Pro Asn Leu Ser Arg Arg Phe Gln Tyr Arg Trp Leu Glu Phe Ser
385                 390                 395                 400

Arg Val Ile Gln Gly Thr Thr Thr Leu Leu Pro Gln Trp Asp Lys Cys
                405                 410                 415

Val Asn Phe Ile Glu Ser Ala Leu Pro Tyr Val Val Gly Lys Met Phe
                420                 425                 430

Val Asp Val Tyr Phe Gln Glu Asp Lys Lys Glu Met Met Glu Glu Leu
            435                 440                 445

Val Glu Gly Val Arg Trp Ala Phe Ile Asp Met Leu Glu Lys Glu Asn
    450                 455                 460

Glu Trp Met Asp Ala Gly Thr Lys Arg Lys Ala Lys Glu Lys Ala Arg
465                 470                 475                 480

Ala Val Leu Ala Lys Val Gly Tyr Pro Glu Phe Ile Met Asn Asp Thr
                485                 490                 495

His Val Asn Glu Asp Leu Lys Ala Ile Lys Phe Ser Glu Ala Asp Tyr
                500                 505                 510

Phe Gly Asn Val Leu Gln Thr Arg Lys Tyr Leu Ala Gln Ser Asp Phe
            515                 520                 525

Phe Trp Leu Arg Lys Ala Val Pro Lys Thr Glu Trp Phe Thr Asn Pro
    530                 535                 540

Thr Thr Val Asn Ala Phe Tyr Ser Ala Ser Thr Asn Gln Ile Arg Phe
545                 550                 555                 560

Pro Ala Gly Glu Leu Gln Lys Pro Phe Phe Trp Gly Thr Glu Tyr Pro
                565                 570                 575

Arg Ser Leu Ser Tyr Gly Ala Ile Gly Val Ile Val Gly His Glu Phe
            580                 585                 590

Thr His Gly Phe Asp Asn Asn Gly Arg Lys Tyr Asp Lys Asn Gly Asn
        595                 600                 605

Leu Asp Pro Trp Trp Ser Thr Glu Ser Glu Glu Lys Phe Lys Glu Lys
    610                 615                 620
```

```
Thr Lys Cys Met Ile Asn Gln Tyr Ser Asn Tyr Tyr Trp Lys Lys Ala
625                 630                 635                 640

Gly Leu Asn Val Lys Gly Lys Arg Thr Leu Gly Glu Asn Ile Ala Asp
                645                 650                 655

Asn Gly Gly Leu Arg Glu Ala Phe Arg Ala Tyr Arg Lys Trp Ile Asn
                660                 665                 670

Asp Arg Arg Gln Gly Leu Glu Glu Pro Leu Pro Gly Ile Thr Phe
            675                 680                 685

Thr Asn Asn Gln Leu Phe Phe Leu Ser Tyr Ala His Val Arg Cys Asn
            690                 695                 700

Ser Tyr Arg Pro Glu Ala Ala Arg Glu Gln Val Gln Ile Gly Ala His
705                 710                 715                 720

Ser Pro Pro Gln Phe Arg Val Asn Gly Ala Ile Ser Asn Phe Glu Glu
                725                 730                 735

Phe Gln Lys Ala Phe Asn Cys Pro Pro Asn Ser Thr Met Asn Arg Gly
                740                 745                 750

Met Asp Ser Cys Arg Leu Trp
            755

<210> SEQ ID NO 3
<211> LENGTH: 749
<212> TYPE: PRT
<213> ORGANISM: Homo sapiens

<400> SEQUENCE: 3

Met Glu Ala Glu Thr Gly Ser Ser Val Glu Thr Gly Lys Lys Ala Asn
1               5                   10                  15

Arg Gly Thr Arg Ile Ala Leu Val Val Phe Val Gly Gly Thr Leu Val
                20                  25                  30

Leu Gly Thr Ile Leu Phe Leu Val Ser Gln Gly Leu Leu Ser Leu Gln
                35                  40                  45

Ala Lys Gln Glu Tyr Cys Leu Lys Pro Glu Cys Ile Glu Ala Ala Ala
    50                  55                  60

Ala Ile Leu Ser Lys Val Asn Leu Ser Val Asp Pro Cys Asp Asn Phe
65                  70                  75                  80

Phe Arg Phe Ala Cys Asp Gly Trp Ile Ser Asn Asn Pro Ile Pro Glu
                85                  90                  95

Asp Met Pro Ser Tyr Gly Val Tyr Pro Trp Leu Arg His Asn Val Asp
                100                 105                 110

Leu Lys Leu Lys Glu Leu Leu Glu Lys Ser Ile Ser Arg Arg Arg Asp
            115                 120                 125

Thr Glu Ala Ile Gln Lys Ala Lys Ile Leu Tyr Ser Ser Cys Met Asn
            130                 135                 140

Glu Lys Ala Ile Glu Lys Ala Asp Ala Lys Pro Leu Leu His Ile Leu
145                 150                 155                 160

Arg His Ser Pro Phe Arg Trp Pro Val Leu Glu Ser Asn Ile Gly Pro
                165                 170                 175

Glu Gly Val Trp Ser Glu Arg Lys Phe Ser Leu Leu Gln Thr Leu Ala
                180                 185                 190

Thr Phe Arg Gly Gln Tyr Ser Asn Ser Val Phe Ile Arg Leu Tyr Val
            195                 200                 205

Ser Pro Asp Asp Lys Ala Ser Asn Glu His Ile Leu Lys Leu Asp Gln
    210                 215                 220

Ala Thr Leu Ser Leu Ala Val Arg Glu Asp Tyr Leu Asp Asn Ser Thr
```

```
            225                 230                 235                 240

Glu Ala Lys Ser Tyr Arg Asp Ala Leu Tyr Lys Phe Met Val Asp Thr
                245                 250                 255

Ala Val Leu Leu Gly Ala Asn Ser Ser Arg Ala Glu His Asp Met Lys
                260                 265                 270

Ser Val Leu Arg Leu Glu Ile Lys Ile Ala Glu Ile Met Ile Pro His
                275                 280                 285

Glu Asn Arg Thr Ser Glu Ala Met Tyr Asn Lys Met Asn Ile Ser Glu
                290                 295                 300

Leu Ser Ala Met Ile Pro Gln Phe Asp Trp Leu Gly Tyr Ile Lys Lys
305                 310                 315                 320

Val Ile Asp Thr Arg Leu Tyr Pro His Leu Lys Asp Ile Ser Pro Ser
                325                 330                 335

Glu Asn Val Val Arg Val Pro Gln Tyr Phe Lys Asp Leu Phe Arg
                340                 345                 350

Ile Leu Gly Ser Glu Arg Lys Lys Thr Ile Ala Asn Tyr Leu Val Trp
                355                 360                 365

Arg Met Val Tyr Ser Arg Ile Pro Asn Leu Ser Arg Arg Phe Gln Tyr
                370                 375                 380

Arg Trp Leu Glu Phe Ser Arg Val Ile Gln Gly Thr Thr Thr Leu Leu
385                 390                 395                 400

Pro Gln Trp Asp Lys Cys Val Asn Phe Ile Glu Ser Ala Leu Pro Tyr
                405                 410                 415

Val Val Gly Lys Met Phe Val Asp Val Tyr Phe Gln Glu Asp Lys Lys
                420                 425                 430

Glu Met Met Glu Glu Leu Val Glu Gly Val Arg Trp Ala Phe Ile Asp
                435                 440                 445

Met Leu Glu Lys Glu Asn Glu Trp Met Asp Ala Gly Thr Lys Arg Lys
                450                 455                 460

Ala Lys Glu Lys Ala Arg Ala Val Leu Ala Lys Val Gly Tyr Pro Glu
465                 470                 475                 480

Phe Ile Met Asn Asp Thr His Val Asn Glu Asp Leu Lys Ala Ile Lys
                485                 490                 495

Phe Ser Glu Ala Asp Tyr Phe Gly Asn Val Leu Gln Thr Arg Lys Tyr
                500                 505                 510

Leu Ala Gln Ser Asp Phe Phe Trp Leu Arg Lys Ala Val Pro Lys Thr
                515                 520                 525

Glu Trp Phe Thr Asn Pro Thr Thr Val Asn Ala Phe Tyr Ser Ala Ser
                530                 535                 540

Thr Asn Gln Ile Arg Phe Pro Ala Gly Glu Leu Gln Lys Pro Phe Phe
545                 550                 555                 560

Trp Gly Thr Glu Tyr Pro Arg Ser Leu Ser Tyr Gly Ala Ile Gly Val
                565                 570                 575

Ile Val Gly His Glu Phe Thr His Gly Phe Asp Asn Asn Gly Arg Lys
                580                 585                 590

Tyr Asp Lys Asn Gly Asn Leu Asp Pro Trp Trp Ser Thr Glu Ser Glu
                595                 600                 605

Glu Lys Phe Lys Glu Lys Thr Lys Cys Met Ile Asn Gln Tyr Ser Asn
                610                 615                 620

Tyr Tyr Trp Lys Lys Ala Gly Leu Asn Val Lys Gly Lys Arg Thr Leu
625                 630                 635                 640

Gly Glu Asn Ile Ala Asp Asn Gly Gly Leu Arg Glu Ala Phe Arg Ala
                645                 650                 655
```

```
Tyr Arg Lys Trp Ile Asn Asp Arg Arg Gln Gly Leu Glu Glu Pro Leu
            660                 665                 670

Leu Pro Gly Ile Thr Phe Thr Asn Asn Gln Leu Phe Phe Leu Ser Tyr
            675                 680                 685

Ala His Val Arg Cys Asn Ser Tyr Arg Pro Glu Ala Ala Arg Glu Gln
            690                 695                 700

Val Gln Ile Gly Ala His Ser Pro Pro Gln Phe Arg Val Asn Gly Ala
705                 710                 715                 720

Ile Ser Asn Ser Glu Glu Phe Gln Lys Ala Phe Asn Cys Pro Pro Asn
            725                 730                 735

Ser Thr Met Asn Arg Gly Met Asp Ser Cys Arg Leu Trp
            740                 745

<210> SEQ ID NO 4
<211> LENGTH: 718
<212> TYPE: PRT
<213> ORGANISM: Artificial Sequence
<220> FEATURE:
<223> OTHER INFORMATION: Soluble PHEX conjugate

<400> SEQUENCE: 4

Ser Gly Asp Asp Asp Asp Asp Asp Asp Asp Ser Gly Ser Leu
1               5                   10                  15

Gln Ala Lys Gln Glu Tyr Cys Leu Lys Pro Glu Cys Ile Glu Ala Ala
            20                  25                  30

Ala Ala Ile Leu Ser Lys Val Asn Leu Ser Val Asp Pro Cys Asp Asn
            35                  40                  45

Phe Phe Arg Phe Ala Cys Asp Gly Trp Ile Ser Asn Asn Pro Ile Pro
50                  55                  60

Glu Asp Met Pro Ser Tyr Gly Val Tyr Pro Trp Leu Arg His Asn Val
65                  70                  75                  80

Asp Leu Lys Leu Lys Glu Leu Leu Glu Lys Ser Ile Ser Arg Arg Arg
            85                  90                  95

Asp Thr Glu Ala Ile Gln Lys Ala Lys Ile Leu Tyr Ser Ser Cys Met
            100                 105                 110

Asn Glu Lys Ala Ile Glu Lys Ala Asp Ala Lys Pro Leu Leu His Ile
            115                 120                 125

Leu Arg His Ser Pro Phe Arg Trp Pro Val Leu Glu Ser Asn Ile Gly
            130                 135                 140

Pro Glu Gly Val Trp Ser Glu Arg Lys Phe Ser Leu Leu Gln Thr Leu
145                 150                 155                 160

Ala Thr Phe Arg Gly Gln Tyr Ser Asn Ser Val Phe Ile Arg Leu Tyr
            165                 170                 175

Val Ser Pro Asp Asp Lys Ala Ser Asn Glu His Ile Leu Lys Leu Asp
            180                 185                 190

Gln Ala Thr Leu Ser Leu Ala Val Arg Glu Asp Tyr Leu Asp Asn Ser
            195                 200                 205

Thr Glu Ala Lys Ser Tyr Arg Asp Ala Leu Tyr Lys Phe Met Val Asp
            210                 215                 220

Thr Ala Val Leu Leu Gly Ala Asn Ser Ser Arg Ala Glu His Asp Met
225                 230                 235                 240

Lys Ser Val Leu Arg Leu Glu Ile Lys Ile Ala Glu Ile Met Ile Pro
            245                 250                 255

His Glu Asn Arg Thr Ser Glu Ala Met Tyr Asn Lys Met Asn Ile Ser
            260                 265                 270
```

```
Glu Leu Ser Ala Met Ile Pro Gln Phe Asp Trp Leu Gly Tyr Ile Lys
            275                 280                 285

Lys Val Ile Asp Thr Arg Leu Tyr Pro His Leu Lys Asp Ile Ser Pro
290                 295                 300

Ser Glu Asn Val Val Arg Val Pro Gln Tyr Phe Lys Asp Leu Phe
305                 310                 315                 320

Arg Ile Leu Gly Ser Glu Arg Lys Lys Thr Ile Ala Asn Tyr Leu Val
                325                 330                 335

Trp Arg Met Val Tyr Ser Arg Ile Pro Asn Leu Ser Arg Arg Phe Gln
            340                 345                 350

Tyr Arg Trp Leu Glu Phe Ser Arg Val Ile Gln Gly Thr Thr Thr Leu
        355                 360                 365

Leu Pro Gln Trp Asp Lys Cys Val Asn Phe Ile Glu Ser Ala Leu Pro
    370                 375                 380

Tyr Val Gly Lys Met Phe Val Asp Val Tyr Phe Gln Glu Asp Lys
385                 390                 395                 400

Lys Glu Met Met Glu Glu Leu Val Glu Gly Val Arg Trp Ala Phe Ile
                405                 410                 415

Asp Met Leu Glu Lys Glu Asn Glu Trp Met Asp Ala Gly Thr Lys Arg
            420                 425                 430

Lys Ala Lys Glu Lys Ala Arg Ala Val Leu Ala Lys Val Gly Tyr Pro
        435                 440                 445

Glu Phe Ile Met Asn Asp Thr His Val Asn Glu Asp Leu Lys Ala Ile
    450                 455                 460

Lys Phe Ser Glu Ala Asp Tyr Phe Gly Asn Val Leu Gln Thr Arg Lys
465                 470                 475                 480

Tyr Leu Ala Gln Ser Asp Phe Phe Trp Leu Arg Lys Ala Val Pro Lys
                485                 490                 495

Thr Glu Trp Phe Thr Asn Pro Thr Thr Val Asn Ala Phe Tyr Ser Ala
            500                 505                 510

Ser Thr Asn Gln Ile Arg Phe Pro Ala Gly Glu Leu Gln Lys Pro Phe
        515                 520                 525

Phe Trp Gly Thr Glu Tyr Pro Arg Ser Leu Ser Tyr Gly Ala Ile Gly
    530                 535                 540

Val Ile Val Gly His Glu Phe Thr His Gly Phe Asp Asn Asn Gly Arg
545                 550                 555                 560

Lys Tyr Asp Lys Asn Gly Asn Leu Asp Pro Trp Trp Ser Thr Glu Ser
                565                 570                 575

Glu Glu Lys Phe Lys Glu Lys Thr Lys Cys Met Ile Asn Gln Tyr Ser
            580                 585                 590

Asn Tyr Tyr Trp Lys Lys Ala Gly Leu Asn Val Lys Gly Lys Arg Thr
        595                 600                 605

Leu Gly Glu Asn Ile Ala Asp Asn Gly Gly Leu Arg Glu Ala Phe Arg
    610                 615                 620

Ala Tyr Arg Lys Trp Ile Asn Asp Arg Arg Gln Gly Leu Glu Glu Pro
625                 630                 635                 640

Leu Leu Pro Gly Ile Thr Phe Thr Asn Asn Gln Leu Phe Phe Leu Ser
                645                 650                 655

Tyr Ala His Val Arg Cys Asn Ser Tyr Arg Pro Glu Ala Ala Arg Glu
            660                 665                 670

Gln Val Gln Ile Gly Ala His Ser Pro Pro Gln Phe Arg Val Asn Gly
        675                 680                 685
```

```
Ala Ile Ser Asn Phe Glu Glu Phe Gln Lys Ala Phe Asn Cys Pro Pro
        690                 695                 700
Asn Ser Thr Met Asn Arg Gly Met Asp Ser Cys Arg Leu Trp
705                 710                 715

<210> SEQ ID NO 5
<211> LENGTH: 1524
<212> TYPE: DNA
<213> ORGANISM: Artificial Sequence
<220> FEATURE:
<223> OTHER INFORMATION: Encoding soluble alkaline phosphatase

<400> SEQUENCE: 5
ggatccacca tgatttcacc attcttagta ctggccattg gcacctgcct tactaactcc      60
ttagtgccag agaaagagaa agaccccaag tactggcgag accaagcgca agagacactg    120
aaatatgccc tggagcttca gaagctcaac accaacgtgg ctaagaatgt catcatgttc    180
ctgggagatg ggatgggtgt ctccacagtg acggctgccc gcatcctcaa gggtcagctc    240
caccacaacc tggggagga ccaggctg agatggaca agttcccctt cgtggccctc         300
tccaagacgt acaacaccaa tgcccaggtc cctgacagcg ccggcaccgc caccgcctac    360
ctgtgtgggg tgaaggccaa tgagggcacc gtggggtaa gcgcagccac tgagcgttcc     420
cggtgcaaca ccacccaggg gaacgaggtc acctccatcc tgcgctgggc caaggacgct    480
gggaaatctg tgggcattgt gaccaccacg agagtgaacc atgccacccc cagcgccgcc    540
tacgcccact cggctgaccg ggactggtac tcagacaacg agatgccccc tgaggccttg    600
agccagggct gtaaggacat cgcctaccag ctcatgcata acatcaggga cattgacgtg    660
atcatggggg gtgccggaa atacatgtac cccaagaata aaactgatgt ggagtatgag    720
agtgacgaga aagccagggg cacgaggctg gacggcctgg acctcgttga cacctggaag   780
agcttcaaac cgagatacaa gcactccac ttcatctgga accgcacgga actcctgacc     840
cttgaccccc acaatgtgga ctacctattg ggtctcttcg agccagggga catgcagtac   900
gagctgaaca ggaacaacgt gacggacccg tcactctccg agatggtggt ggtggccatc    960
cagatcctgc ggaagaaccc caaaggcttc ttcttgctgg tggaaggagg cagaattgac   1020
cacgggcacc atgaaggaaa agccaagcag gccctgcatg aggcggtgga gatggaccgg   1080
gccatcgggc aggcaggcag cttgacctcc tcggaagaca ctctgaccgt ggtcactgcg   1140
gaccattccc acgtcttcac atttggtgga tacacccccc gtggcaactc tatctttggt   1200
ctggcccca tgctgagtga cacagacaag aagcccttca ctgccatcct gtatggcaat   1260
gggcctggct acaaggtggt gggcggtgaa cgagagaatg tctccatggt ggactatgct   1320
cacaacaact accaggcgca gtctgctgtg ccctgcgcc acgagaccca cggcggggag    1380
gacgtggccg tcttctccaa gggccccatg gcgcacctgc tgcacggcgt ccacgagcag   1440
aactacgtcc ccacgtgat ggcgtatgca gcctgcatcg gggccaacct cggccactgt    1500
gctcctgcca gctcgtagtc taga                                              1524

<210> SEQ ID NO 6
<211> LENGTH: 502
<212> TYPE: PRT
<213> ORGANISM: Artificial Sequence
<220> FEATURE:
<223> OTHER INFORMATION: Soluble alkaline phosphatase

<400> SEQUENCE: 6

Met Ile Ser Pro Phe Leu Val Leu Ala Ile Gly Thr Cys Leu Thr Asn
```

```
1               5                   10                  15
Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
                35                  40                  45

Asn Val Ala Lys Asn Val Ile Met Phe Leu Gly Asp Gly Met Gly Val
            50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
            115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
                195                 200                 205

Met His Asn Ile Arg Asp Ile Asp Val Ile Met Gly Gly Gly Arg Lys
            210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430
```

```
Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser
            500

<210> SEQ ID NO 7
<211> LENGTH: 1554
<212> TYPE: DNA
<213> ORGANISM: Artificial Sequence
<220> FEATURE:
<223> OTHER INFORMATION: Encoding soluble alkaline phosphatase conjugate

<400> SEQUENCE: 7
ggatccacca tgatttcacc attcttagta ctggccattg cacctgcct tactaactcc      60
ttagtgccag agaaagagaa agaccccaag tactggcgag accaagcgca agagacactg    120
aaatatgccc tggagcttca gaagctcaac accaacgtgg ctaagaatgt catcatgttc    180
ctgggagatg ggatgggtgt ctccacagtg acggctgccc gcatcctcaa gggtcagctc    240
caccacaacc tggggagga gaccaggctg gagatggaca gttccccctt cgtggccctc    300
tccaagacgt acaacaccaa tgcccaggtc cctgacagcg ccggcaccgc caccgcctac    360
ctgtgtgggg tgaaggccaa tgagggcacc gtggggtaa gcgcagccac tgagcgttcc    420
cggtgcaaca ccacccaggg gaacgaggtc acctccatcc tgcgctgggc caaggacgct    480
gggaaatctg tgggcattgt gaccaccacg agagtgaacc atgccacccc cagcgccgcc    540
tacgcccact cggctgaccg ggactggtac tcagacaacg agatgccccc tgaggccttg    600
agccagggct gtaaggacat cgcctaccag ctcatgcata acatcaggga cattgacgtg    660
atcatggggg gtggccggaa atacatgtac cccaagaata aaactgatgt ggagtatgag    720
agtgacgaga agccaggggc acgaggctg acggcctgg acctcgttga cacctggaag    780
agcttcaaac cgagatacaa gcactcccac ttcatctgga accgcacgga actcctgacc    840
cttgaccccc acaatgtgga ctacctattg ggtctcttcg agccagggga catgcagtac    900
gagctgaaca ggaacaacgt gacggacccg tcactctccg agatggtggt ggtggccatc    960
cagatcctgc ggaagaaccc caaaggcttc ttcttgctgg tggaaggagg cagaattgac   1020
cacgggcacc atgaaggaaa agccaagcag gccctgcatg aggcggtgga gatggaccgg   1080
gccatcgggc aggcaggcag cttgacctcc tcggaagaca ctctgaccgt ggtcactgcg   1140
gaccattccc acgtcttcac atttggtgga tacacccccc gtggcaactc tatctttggt   1200
ctggccccca tgctgagtga cacagacaag aagcccttca ctgccatcct gtatggcaat   1260
gggcctggct acaaggtggt gggcggtgaa cgagagaatg tctccatggt ggactatgct   1320
cacaacaact accaggcgca gtctgctgtg cccctgcgcc acgagaccca cggcggggag   1380
gacgtggccg tcttctccaa gggccccatg gcgcacctgc tgcacggcgt ccacgagcag   1440
aactacgtcc ccacgtgat ggcgtatgca gcctgcatcg gggccaacct cggccactgt   1500
gctcctgcca gctcggatga cgacgatgat gacgatgatg acgactagtc taga         1554
```

-continued

```
<210> SEQ ID NO 8
<211> LENGTH: 512
<212> TYPE: PRT
<213> ORGANISM: Artificial Sequence
<220> FEATURE:
<223> OTHER INFORMATION: Soluble alkaline phosphatase conjugate

<400> SEQUENCE: 8

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
```

```
                370               375               380
Phe Gly Gly Tyr Thr Pro Arg Gly Asn Ser Ile Phe Gly Leu Ala Pro
385               390               395               400

Met Leu Ser Asp Thr Asp Lys Lys Pro Phe Thr Ala Ile Leu Tyr Gly
              405               410               415

Asn Gly Pro Gly Tyr Lys Val Val Gly Gly Glu Arg Glu Asn Val Ser
          420               425               430

Met Val Asp Tyr Ala His Asn Asn Tyr Gln Ala Gln Ser Ala Val Pro
              435               440               445

Leu Arg His Glu Thr His Gly Gly Glu Asp Val Ala Val Phe Ser Lys
          450               455               460

Gly Pro Met Ala His Leu Leu His Gly Val His Glu Gln Asn Tyr Val
465               470               475               480

Pro His Val Met Ala Tyr Ala Ala Cys Ile Gly Ala Asn Leu Gly His
              485               490               495

Cys Ala Pro Ala Ser Ser Asp Asp Asp Asp Asp Asp Asp Asp
          500               505               510

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide

<400> SEQUENCE: 9
gatccgatga cgatgacgat gacgc                                          25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
ggccgcgtca tcgtcatcgt catcg                                          25

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide

<400> SEQUENCE: 11
gatccgatga cgatgacgat gacgatgacg atgacgc                             37

<210> SEQ ID NO 12
<211> LENGTH: 37
<212> TYPE: DNA
<213> ORGANISM: Artificial Sequence
<220> FEATURE:
<223> OTHER INFORMATION: Oligonucleotide

<400> SEQUENCE: 12
ggccgcgtca tcgtcatcgt catcgtcatc gtcatcg                             37

<210> SEQ ID NO 13
<211> LENGTH: 55
<212> TYPE: DNA
<213> ORGANISM: Artificial Sequence
```

```
<220> FEATURE:
<223> OTHER INFORMATION: Oligonucleotide

<400> SEQUENCE: 13
gatccgatga cgatgacgat gacgatgacg atgacgatga cgatgacgat gacgc            55

<210> SEQ ID NO 14
<211> LENGTH: 55
<212> TYPE: DNA
<213> ORGANISM: Artificial Sequence
<220> FEATURE:
<223> OTHER INFORMATION: Oligonucleotide

<400> SEQUENCE: 14
ggccgcgtca tcgtcatcgt catcgtcatc gtcatcgtca tcgtcatcgt catcg            55

<210> SEQ ID NO 15
<211> LENGTH: 61
<212> TYPE: DNA
<213> ORGANISM: Artificial Sequence
<220> FEATURE:
<223> OTHER INFORMATION: Oligonucleotide

<400> SEQUENCE: 15
gatccgatga cagtagtgag tcatctgaca gtggcagttc aagtgagagc gatggtgacg       60
c                                                                      61

<210> SEQ ID NO 16
<211> LENGTH: 61
<212> TYPE: DNA
<213> ORGANISM: Artificial Sequence
<220> FEATURE:
<223> OTHER INFORMATION: Oligonucleotide

<400> SEQUENCE: 16
ggccgcgtca ccatcgctct cacttgaact gccactgtca gatgactcac tactgtcatc      60
g                                                                      61

<210> SEQ ID NO 17
<211> LENGTH: 52
<212> TYPE: DNA
<213> ORGANISM: Artificial Sequence
<220> FEATURE:
<223> OTHER INFORMATION: Oligonucleotide

<400> SEQUENCE: 17
gatccgattc atctgaagag aaattttgc gtagaattgg aagattcggt gc                52

<210> SEQ ID NO 18
<211> LENGTH: 52
<212> TYPE: DNA
<213> ORGANISM: Artificial Sequence
<220> FEATURE:
<223> OTHER INFORMATION: Oligonucleotide

<400> SEQUENCE: 18
ggccgcaccg aatcttccaa ttctacgcaa aaatttctct tcagatgaat cg              52

<210> SEQ ID NO 19
<211> LENGTH: 58
<212> TYPE: DNA
<213> ORGANISM: Artificial Sequence
<220> FEATURE:
<223> OTHER INFORMATION: Oligonucleotide
```

```
<400> SEQUENCE: 19
gatcctgtta tgaatcacat gaaagcatgg aatcttatga acttaatccc ttcattgc      58

<210> SEQ ID NO 20
<211> LENGTH: 58
<212> TYPE: DNA
<213> ORGANISM: Artificial Sequence
<220> FEATURE:
<223> OTHER INFORMATION: Oligonucleotide

<400> SEQUENCE: 20
ggccgcaatg aagggattaa gttcataaga ttccatgctt tcatgtgatt cataacag      58

<210> SEQ ID NO 21
<211> LENGTH: 46
<212> TYPE: DNA
<213> ORGANISM: Artificial Sequence
<220> FEATURE:
<223> OTHER INFORMATION: Oligonucleotide

<400> SEQUENCE: 21
gatcccagaa tgctgtgtcc tctgaagaaa ccaatgactt taaagc                   46

<210> SEQ ID NO 22
<211> LENGTH: 46
<212> TYPE: DNA
<213> ORGANISM: Artificial Sequence
<220> FEATURE:
<223> OTHER INFORMATION: Oligonucleotide

<400> SEQUENCE: 22
ggccgcttta aagtcattgg tttcttcaga ggacacagca ttctgg                   46

<210> SEQ ID NO 23
<211> LENGTH: 64
<212> TYPE: DNA
<213> ORGANISM: Artificial Sequence
<220> FEATURE:
<223> OTHER INFORMATION: Oligonucleotide

<400> SEQUENCE: 23
gatccggcag tagtgactca tccgaagaaa atggagatga cagttcagaa gaggaggagg    60
aagc                                                                64

<210> SEQ ID NO 24
<211> LENGTH: 64
<212> TYPE: DNA
<213> ORGANISM: Artificial Sequence
<220> FEATURE:
<223> OTHER INFORMATION: Oligonucleotide

<400> SEQUENCE: 24
ggccgcttcc tcctcctctt ctgaactgtc atctccattt tcttcggatg agtcactact    60
gccg                                                                64

<210> SEQ ID NO 25
<211> LENGTH: 61
<212> TYPE: DNA
<213> ORGANISM: Artificial Sequence
<220> FEATURE:
<223> OTHER INFORMATION: Oligonucleotide

<400> SEQUENCE: 25
gatcccgcaa aggattctac aagagaaagc agtgcaaacc ttcccgtggc cgcaagcgtg    60
``` c                                                                                         61

<210> SEQ ID NO 26
<211> LENGTH: 61
<212> TYPE: DNA
<213> ORGANISM: Artificial Sequence
<220> FEATURE:
<223> OTHER INFORMATION: Oligonucleotide

<400> SEQUENCE: 26
ggccgcacgc ttgcggccac gggaaggttt gcactgcttt ctcttgtaga atcctttgcg    60
g                                                                                          61

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide

<400> SEQUENCE: 27
agtcgggatc cggaacaagc agcgtgttct ac                                                         32

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide

<400> SEQUENCE: 28
agatcgcggc cgctcaattg tgcacggtgt gattaaagg                                                  39

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide

<400> SEQUENCE: 29
ccggagatga cgatgacgat gacgatgacg atgact                                                     36

<210> SEQ ID NO 30
<211> LENGTH: 36
<212> TYPE: DNA
<213> ORGANISM: Artificial Sequence
<220> FEATURE:
<223> OTHER INFORMATION: Oligonucleotide

<400> SEQUENCE: 30
tctactgcta ctgctactgc tactgctact gaggcc                                                     36

<210> SEQ ID NO 31
<211> LENGTH: 18
<212> TYPE: PRT
<213> ORGANISM: Artificial Sequence
<220> FEATURE:
<223> OTHER INFORMATION: Human fragment of MEPE

<400> SEQUENCE: 31

Asp Asp Ser Ser Glu Ser Ser Asp Ser Gly Ser Ser Ser Glu Ser Asp
1               5                   10                  15

Gly Asp

```
<210> SEQ ID NO 32
<211> LENGTH: 15
<212> TYPE: PRT
<213> ORGANISM: Artificial Sequence
<220> FEATURE:
<223> OTHER INFORMATION: Human fragment of Statherin

<400> SEQUENCE: 32

Asp Ser Ser Glu Glu Lys Phe Leu Arg Arg Ile Gly Arg Phe Gly
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Human fragment of MGP

<400> SEQUENCE: 33

Cys Tyr Glu Ser His Glu Ser Met Glu Ser Tyr Glu Leu Asn Pro Phe
1               5                   10                  15

Ile

<210> SEQ ID NO 34
<211> LENGTH: 13
<212> TYPE: PRT
<213> ORGANISM: Artificial Sequence
<220> FEATURE:
<223> OTHER INFORMATION: Human fragment of OPN

<400> SEQUENCE: 34

Gln Asn Ala Val Ser Ser Glu Glu Thr Asn Asp Phe Lys
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Human fragment of BSP2

<400> SEQUENCE: 35

Gly Ser Ser Asp Ser Ser Glu Glu Asn Gly Asp Asp Ser Ser Glu Glu
1               5                   10                  15

Glu Glu

<210> SEQ ID NO 36
<211> LENGTH: 18
<212> TYPE: PRT
<213> ORGANISM: Artificial Sequence
<220> FEATURE:
<223> OTHER INFORMATION: Human fragment of IGFBP5

<400> SEQUENCE: 36

Arg Lys Gly Phe Tyr Lys Arg Lys Gln Cys Lys Pro Ser Arg Gly Arg
1               5                   10                  15

Lys Arg

<210> SEQ ID NO 37
<211> LENGTH: 151
<212> TYPE: PRT
<213> ORGANISM: Artificial Sequence
<220> FEATURE:
<223> OTHER INFORMATION: Collagen binding domain of staphilococcus
```

-continued aureus collagen adhesin M81736

<400> SEQUENCE: 37

Gly Thr Ser Ser Val Phe Tyr Tyr Lys Thr Gly Asp Met Leu Pro Glu
1               5                   10                  15

Asp Thr Thr His Val Arg Trp Phe Leu Asn Ile Asn Asn Glu Lys Ser
            20                  25                  30

Tyr Val Ser Lys Asp Ile Thr Ile Lys Asp Gln Ile Gln Gly Gly Gln
        35                  40                  45

Gln Leu Asp Leu Ser Thr Leu Asn Ile Asn Val Thr Gly Thr His Ser
    50                  55                  60

Asn Tyr Tyr Ser Gly Gln Ser Ala Ile Thr Asp Phe Glu Lys Ala Phe
65              70                  75                  80

Pro Gly Ser Lys Ile Thr Val Asp Asn Thr Lys Asn Thr Ile Asp Val
                85                  90                  95

Thr Ile Pro Gln Gly Tyr Gly Ser Tyr Asn Ser Phe Ser Ile Asn Tyr
            100                 105                 110

Lys Thr Lys Ile Thr Asn Glu Gln Gln Lys Glu Phe Val Asn Asn Ser
        115                 120                 125

Gln Ala Trp Tyr Gln Glu His Gly Lys Glu Glu Val Asn Gly Lys Ser
    130                 135                 140

Phe Asn His Thr Val His Asn
145                 150

<210> SEQ ID NO 38
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 38
cagtcaaggt ctcttatccg gaagtctcca agctaaacag g         41

<210> SEQ ID NO 39
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 39
ctgtttagct tggagacttc cggataagag accttgactg g         41

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 40
gataaagcag gtcttggggt gcacc                           25

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 41

-continued

```
gttggcatct gtcacgggct tgtgg                                          25
```

<210> SEQ ID NO 42
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 42

```
tggatccacc atgatttcac cattcttagt ac                                  32
```

<210> SEQ ID NO 43
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 43

```
ttctagacta cgagctggca ggagcacagt ggccg                               35
```

<210> SEQ ID NO 44
<211> LENGTH: 65
<212> TYPE: DNA
<213> ORGANISM: Artificial Sequence
<220> FEATURE:
<223> OTHER INFORMATION: Oligonucleotide primer

<400> SEQUENCE: 44

```
ttctagacta gtcgtcatca tcgtcatcat cgtcgtcatc cgagctggca ggagcacagt    60
ggccg                                                                65
```

<210> SEQ ID NO 45
<211> LENGTH: 5
<212> TYPE: PRT
<213> ORGANISM: Artificial Sequence
<220> FEATURE:
<223> OTHER INFORMATION: Fragment surrounding cleavage site

<400> SEQUENCE: 45

Ser Leu Gln Ala Lys
1               5

<210> SEQ ID NO 46
<211> LENGTH: 11
<212> TYPE: PRT
<213> ORGANISM: Artificial Sequence
<220> FEATURE:
<223> OTHER INFORMATION: Fragment surrounding cleavage site

<400> SEQUENCE: 46

Thr Ser Asp Lys Thr His Ser Leu Gln Ala Lys
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Fragment surrounding cleavage site

<400> SEQUENCE: 47

Ser Val Ser Leu Gln Ala Lys
1               5

```
<210> SEQ ID NO 48
<211> LENGTH: 19
<212> TYPE: PRT
<213> ORGANISM: Artificial Sequence
<220> FEATURE:
<223> OTHER INFORMATION: Fragment surrounding cleavage site

<400> SEQUENCE: 48

Ser Gly Asp Asp Asp Asp Asp Asp Asp Asp Asp Ser Gly Ser Leu
1               5                   10                  15

Gln Ala Lys

<210> SEQ ID NO 49
<211> LENGTH: 14
<212> TYPE: PRT
<213> ORGANISM: Artificial Sequence
<220> FEATURE:
<223> OTHER INFORMATION: Fragment surrounding cleavage site

<400> SEQUENCE: 49

Ser Asp Asp Asp Asp Asp Asp Tyr Val Ser Leu Gln Ala Lys
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Fragment surrounding cleavage site

<400> SEQUENCE: 50

Arg Thr Val Val Lys Arg Ser Val
1               5
```

BONE DELIVERY CONJUGATES AND METHOD OF USING SAME TO TARGET PROTEINS TO BONE

CROSS REFERENCE TO RELATED APPLICATIONS

This application claims priority on U.S. provisional applications Nos. 60/563,828 filed on Apr. 21, 2004, 60/590,347 filed on Jul. 23, 2004, and 60/614,984 filed on Oct. 4, 2004. All documents above are herein incorporated by reference.

REFERENCE TO A SEQUENCE LISTING

A Sequence Listing is provided in this patent document as a .txt file entitled, "50694_002004_Amended_Sequence_Listing.txt", created Apr. 7, 2010 (size 44.6 kB). The content of this file is hereby incorporated by reference.

FIELD OF THE INVENTION

The present invention relates to bone delivery conjugates and method of using same to target proteins to bone. More specifically, the present invention relates to bone delivery compositions comprising peptide motifs, engineered within the structure of a protein through recombinant DNA technology to promote binding to bone matrix.

BACKGROUND OF THE INVENTION

Technological advances in molecular biology, recombinant protein production and large scale protein purification have allowed the production of large amounts of proteins now used as biopharmaceuticals. For example, monoclonal antibodies and soluble forms of the TNF-a receptor have been used in the treatment of autoimmune diseases such as Crohn's disease or severe forms of psoriasis (1). Another example of use of recombinant protein is enzyme replacement therapy (ERT). ERT has been used to treat lysosomal storage diseases. This group of genetic disorders is characterized by the loss of function of lysosome enzymes resulting in severe somatic, and sometimes neuronal, pathologies. In ERT for these diseases, the patients are infused with large doses of normal enzymes. These infused enzymes are then internalized from circulation via cell surface receptors (mannose-6 phosphate receptor) and enter the endocytic pathway on their way to their site of action, the lysosome. Not all attempts to treat genetic disorders through ERT have been successful.

Hypophosphatasia is a rare, heritable type of rickets or osteomalacia that occurs with an incidence of 1 per 100,000 births for the more severe form of the disease. Milder forms are more prevalent. In this inborn metabolism defect, mutations inactivate the gene that encodes the tissue-nonspecific isoenzyme of alkaline phosphatase. It is characterized biochemically by subnormal alkaline phosphatase activity in serum. Alkaline phosphatase deficiency in osteoblasts and chondrocytes impairs skeletal mineralization, leading to rickets or osteomalacia.

There is a very broad range of expressivity of hypophosphatasia, spanning from a perinatal form often causing stillbirth from an unmineralized skeleton, to a milder form featuring only premature loss of teeth. Severely affected infants and children inherit hypophosphatasia as an autosomal recessive trait. There are four main forms of the disease: perinatal, infantile, childhood and adult. Perinatal hypophosphatasia manifests during gestation and most affected newborns survive only briefly. Infantile hypophosphatasia becomes clinically apparent before 6 months of age. About 50% of patients die within a year. Childhood hypophosphatasia varies greatly in severity but most of these patients will suffer from skeletal symptoms throughout their life. Adult hypophosphatasia appears during middle age, with symptoms such as painful recurrent stress fractures having poor healing.

Osteoblasts and chondrocytes are normally rich in tissue-nonspecific alkaline phosphatase where it is attached to the cell surface. In hypophosphatasia, the lack of alkaline phosphatase activity results in the extracellular accumulation of three phosphorus-compounds believed to be substrates of the enzyme: phosphoethanolamine (PEA), inorganic pyrophosphate (PPi) and pyridoxal 5'-phosphate (PLP). PPi is an inhibitor of hydroxyapatite crystal growth, and PPi build-up in the disease accounts for the impaired skeletal mineralization. Consequently, providing active enzyme to patients suffering from hypophosphatasia will decrease extracellular PPi levels and improve skeletal mineralization.

Currently, there is no established medical therapy for hypophosphatasia. Trials of enzyme replacement using intravenous infusions of alkaline phosphatase have failed. It appears that alkaline phosphatase activity must be increased not in circulation but in the skeleton itself. This hypothesis was confirmed recently by bone marrow transplantation. Unfortunately, the benefits of the transplantation lasted only for a short period of time due to poor engraftment.

There is a therefore a need to provide enzyme replacement therapy approach to provide active enzyme to the skeleton of patients suffering from hypophosphatasia.

Bone-targeted proteins could be useful not only for the treatment or prevention of hypophosphatasia (loss of function of alkaline phosphatase) but also for the treatment or prevention of other genetic diseases characterized by defective enzymatic activity involved in bone metabolism, such as X-linked hypophosphatemic rickets (XLH) (loss of function of phosphate regulating gene with homology to endopeptidases on the X chromosome (PHEX)).

XLH is the most prevalent of the familial hypophosphatemias (OMIM 307800, 307810). It is characterized by reduced phosphate reuptake in the kidney, hypophosphatemia, normocalcemia, normal to low plasma 1,25-dihydroxyvitamin D3 (1,25(OH)2D, calcitriol) levels, normal parathyroid gland function and elevated plasma alkaline phosphatase activity. These changes are associated with growth retardation, lower extremity deformity, radiologic and histomorphometric evidence of rickets and osteomalacia. This disease appears to result from combined renal defects in tubular phosphate reabsorption and vitamin D metabolism, as well as a functional disorder in bone and teeth. XLH results from inactivating mutations in the PHEX gene, a member of the zinc metallopeptidase family of type 11 integral membrane glycoproteins. These mutations prevent the expression of a functional PHEX enzyme at the cell surface of osteoblasts. As of now, treatment of XLH patients is restricted to supplementation with oral inorganic phosphate (Pi) supplements in four or five divided doses per day, and co-administration of 1,25(OH)2D to compensate for the inappropriate synthesis of 1,25(OH)2D. Such high doses of phosphate frequently cause gastrointestinal intolerances, particularly diarrhea, leading to patient non-compliance. On the one hand, the phosphate load carries the risk of provoking secondary hyperparathyroidism (which may be severe enough to necessitate parathyroidectomy) while on the other hand, administration of excess 1,25(OH)2D may lead to hypercalciuria, hypercalcemia and nephrocalcinosis.

Useful ERT for XLH would therefore seek to replace the defective PHEX enzyme in XLH patients with a functional enzyme obtained through recombinant DNA technology. As the normal PHEX enzyme is anchored in osteoblast plasma membrane by a hydrophobic peptide, the natural form of PHEX cannot be produced and purified in sufficient quantities to be used in a pharmaceutical preparation. To circumvent the problem, a soluble form of recombinant PHEX (or sPHEX) was engineered and produced in cell cultures, purified and formulated for intravenous (IV) administration (WO 00/50580). sPHEX was then injected in Hyp mice, a mouse model for XLH, as described in co-pending U.S. application Ser. No. 10/362,259. Improvement of several bone related serum parameter were observed including a reduction of the abnormally high levels of serum alkaline phosphatase. Although these experiments were successful, it was believed that the efficacy of therapeutic sPHEX might be enhanced if the recombinant protein was modified so as to promote its binding to bone minerals.

There is therefore a need for means to successfully target proteins to bone matrix.

Biphosphonates are known to present high affinity binding to hydroxyapatite (HA), and has been used to target small molecules (4) and proteins (5) to bones. However this strategy requires chemical modifications of the purified proteins, and presents several disadvantages including possible interference with protein activity and additional purification steps.

Another strategy to target small molecules to bone has been to conjugate these entities to acidic peptides such as poly-Asp (6). This strategy was developed after the observation that several proteins synthesized by osteoblasts, the bone forming cells, bind to bone matrix through sequences particularly rich in acidic amino acid residues (Asp and Glu). This is the case of osteopontin (7) and bone sialoprotein, two noncollagenous proteins. Hence acidic peptides ($E_{2-10}$ and $D_{2-10}$) were used to target small molecules (i.e. methotrexate, FITC, Fmoc, biotin, estradiol) to hydroxyapatite in vitro. Acidic peptides ($E_6$ and $D_{6-10}$) were used to target small molecules (i.e. FITC, Fmoc, estradiol) to hydroxyapatite in vivo. Finally, $E_6$ was shown to confer to BSA, hemoglobin and IgG the ability to bind hydroxyapatite in vitro. In all the above cases, linking of the acidic sequence was performed chemically.

The present invention seeks to meet these needs and other needs.

The present description refers to a number of documents, the content of which is herein incorporated by reference in their entirety.

SUMMARY OF THE INVENTION

The present invention shows that large and complex molecules such as proteins can be fused with acidic peptides to successfully target bone in vivo.

According to a specific embodiment of the present invention there is provided a bone delivery conjugate having a structure selected from the group consisting of: A) X-Dn-Y-protein-Z; and B) Z-protein-Y-Dn-X, wherein X is absent or is an amino acid sequence of at least one amino acid; Y is absent or is an amino acid sequence of at least one amino acid; Z is absent or is an amino acid sequence of at least one amino acid; and Dn is a poly aspartate wherein n=10 to 16. In an other specific embodiment of the present invention, the protein in the bone delivery conjugate is a soluble phosphate regulating gene with homology to endopeptidases on the X chromosome (sPHEX). In an other specific embodiment of the present invention, the structure of the conjugate is: X-Dn-Y-sPHEX-Z. In other specific embodiment of the present invention, the sPHEX has a sequence selected from the group consisting of amino acids 46 to 749 of FIG. 10; 47 to 749 of FIG. 10; 48 to 749 of FIG. 10; 49 to 749 of FIG. 10; 50 to 749 of FIG. 10; 51 to 749 of FIG. 10; 52 to 749 of FIG. 10; 53 to 749 of FIG. 10; and 54 to 749 of FIG. 10. In a specific embodiment of these bone delivery conjugates, n is 10. In an other specific embodiment of this bone delivery conjugate, n is 11. In an other specific embodiment of this bone delivery conjugate, n is 12. In an other specific embodiment of this bone delivery conjugate, n is 13. In an other specific embodiment of this bone delivery conjugate, n is 14. In an other specific embodiment of this bone delivery conjugate, n is 15. In an other specific embodiment of this bone delivery conjugate, n is 16. In a more specific embodiment of the present invention, the sPHEX consists of the sequence of amino acids 46 to 749 of FIG. 10 and n=10.

In another specific embodiment of the present invention, the protein in the conjugate is a soluble alkaline phosphatase (sALP). In an other specific embodiment, the structure of the conjugate is: Z-sALP-X-Dn-Y. In an other specific embodiment, sALP is encoded by the sequence as set forth in FIG. 16A. In an other specific embodiment, sALP has the sequence as set forth in FIG. 16B. In a specific embodiment of these bone delivery conjugates, n is 10. In an other specific embodiment of this bone delivery conjugate, n is 11. In an other specific embodiment of this bone delivery conjugate, n is 12. In an other specific embodiment of this bone delivery conjugate, n is 13. In an other specific embodiment of this bone delivery conjugate, n is 14. In an other specific embodiment of this bone delivery conjugate, n is 15. In an other specific embodiment of this bone delivery conjugate, n is 16. In a more specific embodiment, n=10.

There is also provided an isolated nucleic acid molecule comprising a polynucleotide sequence selected from the group consisting of: a polynucleotide encoding a polypeptide comprising an amino acid sequence as set forth in FIG. 8; a polynucleotide encoding a polypeptide comprising an amino acid sequence as set forth in FIG. 11; a polynucleotide comprising the nucleotide sequence as set forth in FIG. 7; a nucleotide sequence completely complementary to any of the nucleotide sequences in (a), (b) or (c); and a nucleotide sequence which hybridizes under high stringency conditions to any of the nucleotide sequences in (a), (b), (c) or (d), wherein the high stringency conditions comprise: pre-hybridization and hybridization in 6×SSC, 5× Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

There is also provided a recombinant vector comprising said sequence. There is also provided a recombinant host cell comprising said vector.

There is also provided an isolated nucleic acid molecule comprising a polynucleotide sequence selected from the group consisting of: a polynucleotide comprising the nucleotide sequence as set forth in FIG. 17A; a polynucleotide encoding a polypeptide comprising an amino acid sequence as set forth in FIG. 17B; a nucleotide sequence completely complementary to any of the nucleotide sequences in (a) or (b); and a nucleotide sequence which hybridizes under high stringency conditions to any of the nucleotide sequences in (a), (b) or (c), wherein the high stringency conditions comprise: pre-hybridization and hybridization in 6×SSC, 5× Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

There is also provided an isolated nucleic acid molecule encoding a functional soluble PHEX comprising a polynucleotide sequence selected from the group consisting of: a polynucleotide encoding a sPHEX comprising amino acids 54 to 749 as set forth in FIG. 10; a polynucleotide encoding a sPHEX comprising amino acids 53 to 749 as set forth in FIG. 10; a polynucleotide encoding a sPHEX comprising amino acids 52 to 749 as set forth in FIG. 10; a polynucleotide encoding a sPHEX comprising amino acids 51 to 749 as set forth in FIG. 10; a polynucleotide encoding a sPHEX comprising amino acids 50 to 749 as set forth in FIG. 10; a polynucleotide encoding a sPHEX comprising amino acids 49 to 749 as set forth in FIG. 10; a polynucleotide encoding a sPHEX comprising amino acids 48 to 749 as set forth in FIG. 10; a polynucleotide encoding a sPHEX comprising amino acids 47 to 749 as set forth in FIG. 10; a polynucleotide encoding a sPHEX comprising amino acids 46 to 749 as set forth in FIG. 10; a nucleotide sequence completely complementary to any of the nucleotide sequences in (a) to (i); and a nucleotide sequence which hybridizes under high stringency conditions to any of the nucleotide sequences in (a) to (j), wherein the high stringency conditions comprise: pre-hybridization and hybridization in 6×SSC, 5× Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes. In an other embodiment, the isolated nucleic acid molecule further comprises at its 5' end, a polynucleotide encoding a poly-aspartate selected from the group consisting of $D_{10}$ to $D_{16}$.

There is also provided an isolated sPHEX polypeptide comprising a sequence selected from the group consisting of: amino acids 54 to 749 as set for in FIG. 10; amino acids 53 to 749 as set for in FIG. 10; amino acids 52 to 749 as set for in FIG. 10; amino acids 51 to 749 as set for in FIG. 10; amino acids 50 to 749 as set for in FIG. 10; amino acids 49 to 749 as set for in FIG. 10; amino acids 48 to 749 as set for in FIG. 10; amino acids 47 to 749 as set for in FIG. 10; and amino acids 46 to 749 as set for in FIG. 10.

There is also provided a bone delivery composition comprising a bone delivery conjugate of the present invention, and a pharmaceutically acceptable carrier.

There is also provided a method of delivering a protein to bone tissue of a mammal comprising administering to said mammal an effective amount of a bone delivery conjugate as recited of the present invention.

There is also provided a method of delivering sPHEX to bone tissue of a mammal comprising administering to said mammal an effective amount of a bone delivery conjugate of the present invention.

There is also provided a method of delivering ALP to bone tissue of a mammal in need thereof comprising administering to said mammal an effective amount of a bone delivery conjugate of the present invention.

There is also provided a method of treating a condition or disease related to a bone defect characterized by a lack of or an insufficient amount of functional phosphate regulating gene with homology to endopeptidases on the X chromosome (PHEX) comprising administering to a mammal in need thereof a conjugate of the present invention, said conjugate being in a pharmaceutically acceptable carrier. In specific embodiments, the condition or disease is X-linked hypophosphatemic rickets (XLH).

There is also provided a method of treating a condition or disease related to a bone defect characterized by a lack of or an insufficient amount of functional alkaline phosphatase comprising administering to a mammal in need thereof a conjugate of the present invention, said conjugate being in a pharmaceutically acceptable carrier. In specific embodiments, the condition or disease is hypophosphatasia.

There is also provided a method of screening peptides for use in a bone delivery protein-peptide conjugate comprising the steps of: fusing a candidate peptide to a reporter protein to form a protein-peptide conjugate; contacting the conjugate with bone tissue or mineral phase of bone; and wherein the candidate peptide is selected when the presence of the reporter protein on bone tissue or mineral phase of bone is higher when it is conjugated with the candidate peptide than when it is not.

According to a specific embodiment of the present invention there is provided a bone delivery conjugate of a protein fused to a peptide selected from the group consisting of deca-aspartate ($D_{10}$) to hexadeca-aspartate ($D_{16}$).

In specific embodiments of conjugates of the present invention, the sPHEX is fused at its N-terminal to $D_{10}$. In an other specific embodiment, the sPHEX is fused at its N-terminal to $D_{11}$. In an other specific embodiment, the sPHEX is fused at its N-terminal to $D_{12}$. In an other specific embodiment, the sPHEX is fused at its N-terminal to $D_{13}$. In an other specific embodiment, the sPHEX is fused at its N-terminal to $D_{14}$. In an other specific embodiment, the sPHEX is fused at its N-terminal to $D_{15}$. In an other specific embodiment, the sPHEX is fused at its N-terminal to $D_{16}$.

According specific embodiments of conjugates of the present invention, the sALP is fused at its C-terminal to $D_{10}$. In an other specific embodiment, the sALP is fused at its C-terminal $D_{11}$. In an other specific embodiment, the sALP is fused at its C-terminal to $D_{12}$. In an other specific embodiment, the sALP is fused at its C-terminal to $D_{13}$. In an other specific embodiment, the sALP is fused at its C-terminal to $D_{14}$. In an other specific embodiment, the sALP is fused at its C-terminal to $D_{15}$. In an other specific embodiment, the sALP is fused at its C-terminal to $D_{16}$.

It is understood that any functional soluble protein may be used in the conjugate of the present invention. Although results for conjugates comprising one specific sPHEX or sALP of the present invention are presented herein, it is understood that any other functional sPHEX or sALP may be so used.

sPHEX

As used herein sPHEX means any soluble biologically active fragment of PHEX or mutein thereof. Those of skill in the art may prepare expression constructs other than those expressly described herein for optimal production of sPHEX in suitable cell lines transfected therewith. Moreover, skilled artisans may design fragments of cDNA encoding soluble biologically active fragments and muteins of the naturally occurring PHEX which possess the same or similar biological activity to the naturally occurring full-length enzyme.

To create a recombinant source for sPHEX, a large series of expression vectors may be constructed and tested for expression of a PHEX cDNA. Based on transient transfection experiments, as well as stable transfections, an expression construct may be identified that provides a particularly high level of expression.

Without being so limited, any sPHEX comprising at least a native PHEX ectodomain portion starting with the cysteine at position 54 of the sequence presented at FIG. 10 is encompassed by the present invention.

The conjugates according to specific embodiments of the present invention thus are any sPHEX comprising this 54-749 fragment of the native PHEX, preferably the 53-749 native fragment, more preferably the native 52-749 fragment, more preferably the native 51-749 fragment, more preferably the 50-749 native fragment, more preferably the 49-749 native fragment, more preferably the 48-749 native fragment, more preferably the 47-749 native fragment, and more preferably the 46-749 native fragment, along with a poly-aspartate selected from the group consisting of $D_{10}$ to $D_{16}$ fused immediately upstream of this fragment.

The conjugate may further optionally comprise one or more additional amino acids 1) upstream from the poly-aspartate; and/or 2) between the poly-aspartate and the native fragment or functional equivalent. These amino acids may be any amino acid. According to specific embodiments, they may be selected independently from the group consisting of any amino acid except for cysteine, proline and tryptophan namely those amino acids known to induce disulfide bond formation or changes in conformation.

These amino acids may be present in the conjugate when for instance the cloning strategy used to produce it introduces them in these locations.

According to specific cloning strategies, amino acids located upstream of the poly-aspartate in the recombinant cleavable PHEX can be selected according to known parameters so as to provide an adequate substrate for specific enzymes of the secretory pathway (e.g. furin or signal peptidase) of the host cell that will be used to cleave the produced recombinant cleavable PHEXs into a secreted bone targeting sPHEX. The likelihood of a designed sequence being cleaved by the signal peptidase of the host cell can be predicted by an appropriate computer algorithm such as that described in Bendtsen et al. (J Mol Biol. 2004 July 16;340(4):783-95) and available on the Web which takes into account parameters including the following: the amino acids at position −3 and −1 from the cleavage site by the signal peptidase desirably have small and non charged side chains. Preferably, at position −1: Ala, Ser, Gly, Cys, Thr and occasionally Gln, Pro, and Leu. Similarly those at position −3 should preferably be: Ala, Ser, Gly, Cys, Thr, Ile, Leu, Val. Moreover, amino acids in position −6 and −4 from the cleavage site are desirably those capable of inducing the formation of a beta-turn (such as Pro) residues.

The present invention hence encompasses conjugates comprising additional amino acids that may be selected on the basis of the cloning strategy used to produce a cleavable recombinant PHEX. Hence the cleavable recombinant PHEX disclosed in Examples 3 and 4 below contains such additional amino acids upstream of the poly-aspartate and between the poly-aspartate and the native ectodomain sequence. Also, the present invention encompasses a conjugate comprising the secPHEX disclosed in co-pending application Ser. No. WO 02/15918 prepared by fusing NL-1 N-terminal fragment comprising a furin site to the PHEX native ectodomain with the vector pCDNA3/RSV/NL-1-PHEX, and a secPHEX comprising an immunoglobulin fragment at its N-terminal. More particularly, FIG. 12 schematically presents the structure of secPHEXs that comprise additional amino acids upstream of the native 46-749 PHEX ectodomain fragment. Constructs no. 1 to 3 and 5 could be fused to a poly-aspartate and be used as conjugates of the present invention. Construct no. 4 constitutes a conjugate of the present invention: it comprises a $D_{10}$ poly-aspartate and a native ectodomain fragment.

The conjugates of the present invention further also encompass sPHEXs comprising deletions at their C-terminal non detrimental to their enzymatic activity.

Furthermore, the present invention comprises conjugates wherein the poly-aspartate would be attached at the C-terminal of the native PHEX ectodomain fragment.

sALP

ALP is a membrane-bound protein anchored through a glycolipid to its C-terminal. This glycolipid anchor (GPI) is added post translationally after removal of a hydrophobic C-terminal end which serves both as transitional membrane anchor and as a signal for the addition of the GPI. Hence the sALP used in Example 6 herein is constituted of an ALP wherein the first amino acid of the hydrophobic C-terminal sequence, namely alanine, is replaced by a stop codon. The soluble ALP so formed contains all amino acids of the native and thus active anchored form of ALP.

The sALP conjugates according to specific embodiments of the present invention thus are any sALP along with a poly-aspartate selected from the group consisting of $D_{10}$ to $D_{16}$ fused immediately downstream of this fragment.

The conjugate may further optionally comprise one or more additional amino acids 1) upstream from the poly-aspartate; and/or 2) between the poly-aspartate and the native sALP fragment or functional equivalent. This is the case for instance when the cloning strategy used to produce the bone targeting conjugate introduces exogenous amino acids in these locations. However the exogenous amino acids should be selected so as not to provide an additional transamination site. The likelihood of a designed sequence being cleaved by the transaminase of the host cell can be predicted as described by Ikezawa (Biol Pharm. Bull. 2002, 25(4) 409-417).

The conjugates of the present invention further also encompass sALPs comprising deletions at their N-terminal non detrimental to their enzymatic activity.

Furthermore, the present invention comprises conjugates wherein the poly-aspartate would be attached at the N-terminal of the native ALP anchored fragment or its biologically active fragment.

The term "recombinant protein" is used herein to refer to a protein encoded by a genetically manipulated nucleic acid inserted into a prokaryotic or eukaryotic host cell. The nucleic acid is generally placed within a vector, such as a plasmid or virus, as appropriate for the host cell. Although *E. Coli* has been used as a host for expressing the conjugates of the present invention in the Examples presented herein, a person of ordinary skill in the art will understand that a number of other hosts may be used to produce recombinant proteins according to methods that are routine in the art. Representative methods are disclosed in Maniatis, et al. Cold Springs Harbor Laboratory (1989). "Recombinant cleavable protein" as used herein is meant to refer to a recombinant protein that may be cleaved by a host's enzyme so as to produce a secreted/soluble protein.

The term "ectodomain fragment" is meant herein when used in relation to PHEX is meant to refer to PHEX's fragment that is located outside of the cellular membrane when found in its native form.

The term "bone tissue" is used herein to refer to tissue synthesized by osteoblasts composed of an organic matrix containing mostly collagen and mineralized by the deposition of hydroxyapatite crystals.

The fusion proteins comprised in the bone delivery conjugates of the present invention are useful for therapeutic treatment of bone defective conditions by providing an effective amount of the fusion protein to the bone. The fusion protein is provided in the form of a pharmaceutical composition in any standard pharmaceutically acceptable carrier, and is administered by any standard procedure, for example by intravenous injection.

The term "pharmaceutically acceptable carrier" is used herein to refer, when parenteral administration is elected as the route of administration, to pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous solvents include water; water-alcohol solutions; physiological saline; buffered medical parenteral vehicles including sodium chloride solution, Ringer's dextrose solution, dextrose plus sodium chloride solution, fluid and nutrient replenishers; electrolyte replenishers; Ringer's solution containing lactose, or fixed oils.

The term "effective amount" is used herein to refer to the minimal amount of a pharmaceutical composition that should be administered to a mammal in order to achieve a significant therapeutic effect. The dosages will depend on many factors including the mode of administration. Typically, the amount of protein contained within a single dose will be an amount that effectively prevents, delays or treats bone related undesired condition without inducing significant toxicity. In particular, an effective amount of the conjugate and compositions of the present invention will comprise an amount of fusion protein which will cause a significant alleviation of clinical symptoms of the condition.

The effective amount may be given daily, weekly, monthly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount is a dose that ranges from about 1 mg to about 25 grams of the conjugate to be targeted to bone per day, from about 50 mg to about 10 grams of the conjugate to be targeted to bone per day, from about 100 mg to about 5 grams of the conjugate to be targeted to bone per day, about 1 gram of the conjugate to be targeted to bone per day, about 1 mg to about 25 grams of the conjugate to be targeted to bone per week, about 50 mg to about 10 grams of the conjugate to be targeted to bone per week, about 100 mg to about 5 grams of the conjugate to be targeted to bone every other day, and about 1 gram of the conjugate to be targeted to bone once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the protein for delivery to bone is given to the patient, but it is particularly advisable in such cases to begin with low doses to determine if adverse side effects are experienced.

The term "high stringency conditions" are meant to refer to conditions enabling sequences with a high homology to bind. Without being so limited, examples of such conditions are listed In the handbook "*Molecular cloning, a laboratory manual*, second edition of 1989 from Sambrook et al.: 6×SSC or 6×SSPE, Denhardt's reagent or not, 0.5% SDS and the temperature used for obtaining high stringency conditions is most often in around 68° C. (see pages 9.47 to 9.55 of Sambrook) for nucleic acid of 300 to 1500 nucleotides. Although the optimal temperature to be used for a specific nucleic acid probe may be empirically calculated, and although there is room for alternatives in the buffer conditions selected, within these very well known condition ranges, the nucleic acid captured will not vary significantly. Indeed, Sambrook clearly indicates that the "choice depends to a large extent on personal preference" (see page 9.47). Sambrook specifies that the formula to calculate the optimal temperature which varies according to the fraction of guanine and cytosine in the nucleic acid probe and the length of the probe (10 to 20° C. lower than $T_m$ wherein $T_m$=81.5° C.+16.6($\log_{10}$ [Na$^+$])+0.41 (fraction G+C)−0.63(% formamide−(600/l)) (see pages 9.50 and 9.51 of Sambrook).

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 4 presents a chromatographic profile of 280 nm detection of PHEX flow for the SP-Sepharose™ HP (A) and the blue-Sepharose HP (B). Straight line represents buffer ratio;

FIG. 7 shows the nucleotide sequence of a recombinant DNA sequence encoding a protein cleavable so as to produce $D_{10}$-sPHEX (SEQ ID NO: 1);

FIG. 8 shows the amino acid sequence encoded by the $D_{10}$-sPHEX of FIG. 7 (SEQ ID NO: 2);

FIG. 10 shows the amino acid of a native (or membrane-bound) PHEX (SEQ ID NO: 3);

FIG. 11 shows the amino acid sequence (SEQ ID NO: 4) of a $D_{10}$-sPHEX conjugate produced by cleavage of the recombinant cleavable protein of FIG. 8;

FIG. 12 schematically illustrates the structure and activities of various secPHEX constructs, Sequences around or following cleavage sites in these constructs no. 1-5 are also shown (SEQ ID NOs: 45-49, respectively). The furin cleavage site for construct no. 3 is also shown (SEQ ID NO: 50);

FIG. 16 shows A. the nucleotidic sequence (SEQ ID NO: 5) of a soluble alkaline phosphatase; and B. the amino acid sequence (SEQ ID NO: 6) of that soluble alkaline phosphatase;

FIG. 17 shows A. the nucleotidic sequence (SEQ ID NO: 7) encoding a conjugate of the present invention, namely sALP-$D_{10}$; and B. the amino acid sequence (SEQ ID NO: 8) of that conjugate.

DESCRIPTION OF ILLUSTRATIVE EMBODIMENTS

Figure 1:
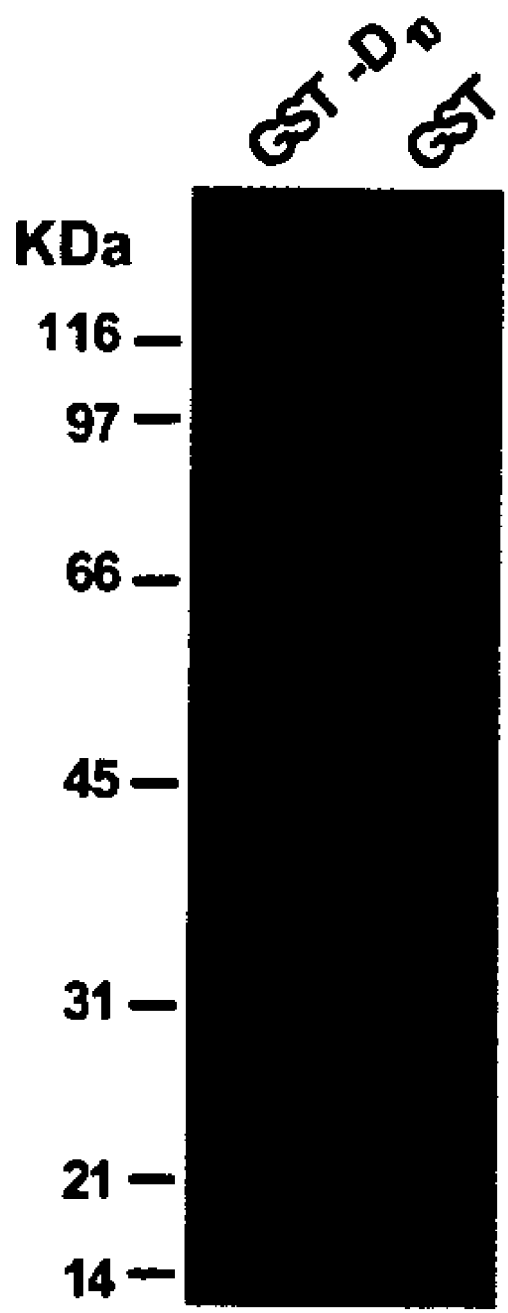
FIG. 1 presents the purity status of GST and GST-$D_{10}$ proteins on an SDS polyacrylamide gel after CL-4B chromatography.

The present invention showed that specific poly-aspartic peptides fused in frame to a protein, as exemplified herein by the gluthatione-S-transferase protein (GST), used as a reporter protein, by sPHEX and by sALP, can significantly increase the bone binding capacity of these proteins.

The present invention is illustrated in further details by the following non-limiting examples.

Table 1 presents the sequence of oligonucleotides used in Examples 1 to 7.

TABLE 1

| \multicolumn{3}{c}{SEQUENCE OF SYNTHETIC OLIGONUCLEOTIDES USED IN EXAMPLES 1 TO 7} | | |
| --- | --- | --- |
| $D_6$ | SEQ ID NO:9 | 5'-GATCCGATGACGATGACGATG ACGC-3'. |
| | SEQ ID NO:10 | 5'-GGCCGCGTCATCGTCATCGTC ATCG-3'. |
| $D_{10}$ | SEQ ID NO:11 | 5'-GATCCGATGACGATGACGATG ACGATGACGATGACGC-3'. |
| | SEQ ID NO:12 | 5'-GGCCGCGTCATCGTCATCGTC ATCGTCATCGTCATCG-3'. |
| $D_{16}$ | SEQ ID NO:13 | 5'-GATCCGATGACGATGACGATG ACGATGACGATGACGATGACGATG ACGATGACGC-3'. |
| | SEQ ID NO:14 | 5'-GGCCGCGTCATCGTCATCGTC ATCGTCATCGTCATCGTCATCGTC ATCGTCATCG-3'. |
| hMEPE | SEQ ID NO:15 | 5'-GATCCGATGACAGTAGTGAGT CATCTGACAGTGGCAGTTCAAGTG AGAGCGATGGTGACGC-3'. |
| | SEQ ID NO:16 | 5'-GGCCGCGTCACCATCGCTCTC ACTTGAACTGCCACTGTCAGATGA CTCACTACTGTCATCG-3'. |
| hStatherin | SEQ ID NO:17 | 5'-GATCCGATTCATCTGAAGAGA AATTTTTGCGTAGAATTGGAAGAT TCGGTGC-3'. |
| | SEQ ID NO:18 | 5'-GGCCGCACCGAATCTTCCAAT TCTACGCAAAAATTTCTCTTCAGA TGAATCG-3'. |
| hMGP | SEQ ID NO:19 | 5'-GATCCTGTTATGAATCACATG AAAGCATGGAATCTTATGAACTTA ATCCCTTCATTGC-3'. |
| | SEQ ID NO:20 | 5'-GGCCGCAATGAAGGGATTAAG TTCATAAGATTCCATGCTTTCATG TGATTCATAACAG-3'. |

TABLE 1-continued

| \multicolumn{3}{c}{SEQUENCE OF SYNTHETIC OLIGONUCLEOTIDES USED IN EXAMPLES 1 TO 7} | | |
| --- | --- | --- |
| hOsteopontin | SEQ ID NO:21 | 5'-GATCCCAGAATGCTGTGTCCT CTGAAGAAACCAATGACTTT AAAGC-3'. |
| | SEQ ID NO:22 | 5'-GGCCGCTTTAAAGTCATTGGT TTCTTCAGAGGACACAGCAT TCTGG-3'. |
| hBSP2 | SEQ ID NO:23 | 5'-GATCCGGCAGTAGTGACTCAT CCGAAGAAATGGAGATGACAGTT CAGAAGAGGAGGAGGAAGC-3'. |
| | SEQ ID NO:24 | 5'-GGCCGCTTCCTCCTCCTCTTC TGAACTGTCATCTCCATTTTCTTC GGATGAGTCACTACTGCCG-3'. |
| hIGFBP5 | SEQ ID NO:25 | 5'-GATCCCGCAAAGGATTCTACA AGAGAAAGCAGTGCAAACCTTCCC GTGGCCGCAAGCGTGC-3'. |
| | SEQ ID NO:26 | 5'-GGCCGCACGCTTGCGGCCACG GAAGGTTTGCACTGCTTTCTCTTG TAGAATCCTTTGCGG-3'. |
| M81736 CBS | SEQ ID NO:27 | 5'-AGTCGGGATCCGGAACAAGCA GCGTGTTCTAC-3'. |
| | SEQ ID NO:28 | 5'-AGATCGCGGCCGCTCAATTGT GCACGGTGTGATTAAAGG-3'. |
| | SEQ ID NO:29 | 5'-CCGGAGATGACGATGACGATG ACGATGACGATGACT-3'. |
| | SEQ ID NO:30 | 3'-TCTACTGCTACTGCTACTGCT ACTGCTACTGAGGCC-5'. |

EXAMPLE 1

Bone Binding of GST-$D_6$, GST-$D_{10}$ and GST-$D_{16}$

Recombinant DNA technology was used to generate a plasmid containing a nucleic acid encoding GST followed in frame by a nucleic acid encoding a $D_6$, $D_{10}$ or $D_{16}$ acidic peptide. To obtain the GST-$D_6$, GST-$D_{10}$ and GST-$D_{16}$ conjugates, the oligonucleotide of SEQ ID NO:9 (see Table 1) was first mixed with the oligonucleotide of SEQ ID NO:10, oligonucleotide of SEQ ID NO:11 mixed with oligonucleotide of SEQ ID NO:12, and oligonucleotide of SEQ ID NO:13 mixed with oligonucleotide of SEQ ID NO:14. This procedure generated duplex oligonucleotides coding for $D_6$, $D_{10}$ and $D_{16}$, respectively, and having extremities compatible with cloning in the pGEX3T-4 plasmid (Pharmacia biotechnology) pre-digested with restriction endonucleases BamHI and NotI. pGEX3T-4 vectors were transformed into AP401 protease minus E. coli bacteria strain (Ion::mini tetR ara-Δlac-pro nalA argEam rifR thiI [F' pro AB lacIq Z M15]).

Positive bacterial colonies were used to seed a 10 ml pre-culture of double YT media and 100 mg/litre ampicilin. Bacteria were grown overnight at 37° C. in an orbital shaker set at 250 rpm. The pre-culture was added to 500 ml of fresh double YT ampicilin media in a 2 litres Erlenmeyer flask. Bacteria were let to grow at 37° C. under orbital shaking until a 595 nm optical density of 0.7 was reached. Protein expression was then induced by adding 500 μl of 0.1 M IPTG solution and the bacteria put back to incubation for 2 hours. Bacteria were spun down at 8000×g for 10 minutes at 4° C. The pellet was suspended in 25 ml of ice-cold PBS containing Complete-EDTA caplet protease inhibitor (Boehringer Mannheim) and frozen at −20° C.

Bacteria cells were thawed and disrupted on ice with 6 pulses of sonication every 50 seconds prior to centrifugation at 12000×g for 10 minutes at 4° C. Supernatant was mixed with 500 µl of GS-4B wet resin (Amersham Pharmacia Biotech) equilibrated with PBS. The resin was kept as a suspension during the overnight incubation at 4° C. The resin was rinsed with PBS until 280 nm optical density was below 0.01. Resin was then laid on an empty column and proteins eluted with 10 mM glutathione dissolved in PBS. The pooled elution fractions were dialyzed against 1 mM sodium $PO_4$ pH 7.4 and 150 mM NaCl. Dialyzed proteins were filtered in a sterile environment on 0.22 µm PES membrane and kept at 4° C. Typically 40 and 60 mg of pure proteins were recovered per litre of culture respectively. FIG. 1 shows an example of an SDS-PAGE analysis of the purified GST and GST-$D_{10}$. Purified proteins were iodinated using Iodo-Beads Iodination Reagent (Pierce).

GST and peptide-fused GST were dialyzed against PBS and concentration set to 2 mg/ml. Iodination reaction was initiated by adding 2 PBS-rinsed Iodo-Beads to 2 mCi of Na125I (100 µCi/µl, ICN) dissolved in 500 µl of PBS. Beads were incubated at room temperature for five minutes before adding 1 mg of dialyzed protein. The iodination reaction proceeded for 15 minutes before the bead was removed and rinsed in 500 ml of PBS. To the final 1.5 ml of iodinated protein solution, 15 µl of 6 mM NaI was added to dilute non-specific radioactivity. The mixture was then desalted using PD-10 gel filtration columns (Amersham Pharmacia Biotech) equilibrated with PBS. Proteins eluted in the void volume. They were concentrated and dialysed against the in vivo buffer (1 mM sodium PO4 pH 7.4 and 150 mM NaCl) using Centriprep-YM10™ cartridges (Amicon). Radioactivity was measured using a gamma radiation counter, protein concentration was assessed by the Bradford assay and $^{125}I$ chemical linkage to proteins was revealed by autoradiography of dried SDS-PAGE. Iodinated samples were kept at 4° C.

Bone Binding Ability of GST-poly-aspartic Peptides Fusion Proteins Compared to that of GST Alone The iodinated GST-fusion proteins were injected to mice under isoflurane anesthesia as an intravenous bolus through the subclavian vein. A dose of 1 mg of iodinated protein/per kg body weight was injected. The maximum dose volume was set at 10 ml/kg. Duration of treatment was sixty minutes. Ten and sixty minutes after injection, blood samples (0.1 to 0.2 ml) were collected via the subclavian vein under anesthesia into serum/gel clotting activator Microvette™ tubes (Sarstedt, #20.1291). At necropsy, blood samples were collected and animals were sacrificed by exsanguination from the heart under isoflurane anesthesia. Organs (kidneys, liver, femurs, tibias and thyroid) were collected, rinsed in saline 0.9% USP, blotted on gauze and transferred into gamma counter tubes. Serum samples and organs were weighted and radioactivity was measured. Results were expressed as percentage of injected dose. Neither $D_{10}$-GST nor $D_{16}$-GST promoted binding to other organs than bone. This showed the specificity of these conjugates to bone (Data not shown).

Figure 2:
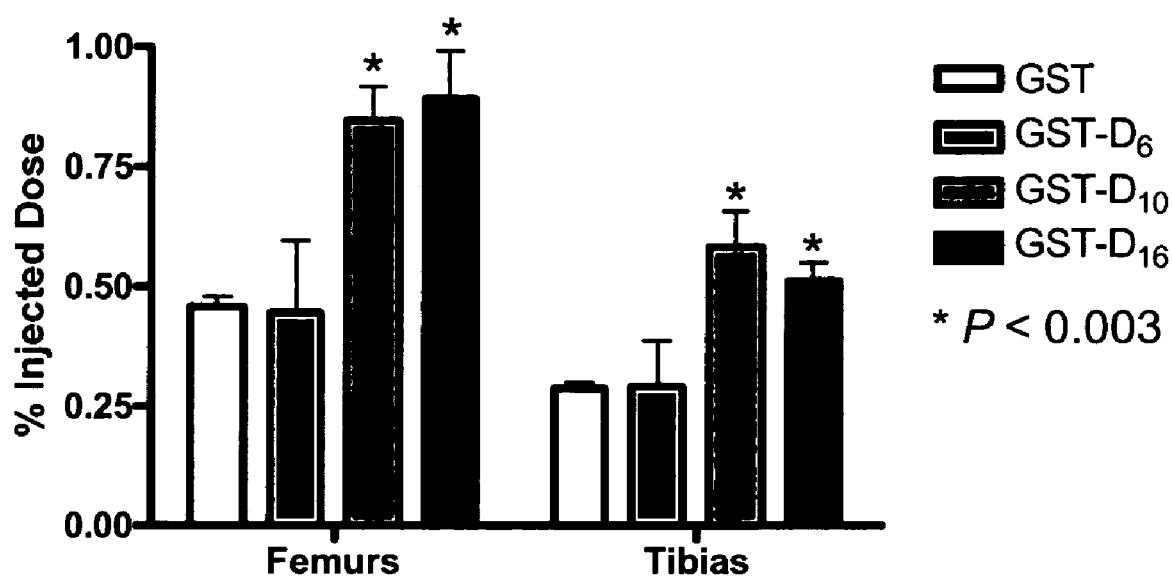
FIG. 2 shows the promotion of GST binding to bone by $D_6$, $D_{10}$ and $D_{16}$ peptide motifs through the percentage of the injected dose of recombinant GST found associated with specific tissues.

FIG. 2 shows that GST-$D_6$ fusion protein did not bind more to tibia or femur than GST alone. In contrast, $D_{10}$ and $D_{16}$ peptide motifs promoted GST binding to bones.

The fact that $D_6$, a peptide shown to successfully deliver small molecules to bone could not successfully deliver a protein, namely GST, to bone shows that it is not predictable whether a specific acidic peptide known to effectively deliver a small molecule to bone will also be effective in delivering a protein to bone.

EXAMPLE 2

Binding Ability of GST Fused with Various Peptides

Human matrix extracellular phosphoglycoprotein (hMEPE) is a protein synthesized by osteoblasts that shows major similarities to a group of bone and teeth mineral matrix phosphor-glycoproteins, proteins known to naturally bind to bone matrix (8). Of particular importance, hMEPE presents at its carboxy-terminus a sequence of 18 amino acid residues (DDSSESSDSGSSSESDGD) (SEQ ID NO: 31) similar to acidic peptides found in dentin phosphorin and dentin sialophosphoprotein, both known to bind to bone matrix (8).

Human Statherin (hStatherin) is a protein synthesized by salivary glands, which similarly to histatin directly modulates hydroxyapatite nucleation and/or growth. Of particular importance, hStatherin presents a sequence of 15 amino acid residues at positions 20 to 34 (DSSEEKFLRRIGRFG) (SEQ ID NO: 32) that was shown to bind tightly to hydroxyapatite (9).

Human Matrix Gla Protein (hMGP) is a protein synthesized by vascular smooth muscle cells and chondrocytes that functions as an inhibitor of hydroxyapatite polymerization by binding to crystal nuclei. Of particular importance, hMGP presents at its amino-terminus a sequence of 17 amino acid residue at positions 19 to 35 of the open reading frame (CYESHESMESYELNPFI) (SEQ ID NO: 33) similar to phosphorylated gamma carboxyglutamic acidic peptides found in osteocalcin known to bind to bone matrix, and thought to promote binding to bone matrix (10).

Human osteopontin (hOPN) is a protein synthesized by osteoblasts that regulates hydroxyapatite crystal growth. This protein belongs to the bone sialophosphoprotein family. Of particular importance, hOPN presents a sequence of 13 amino acid residue (QNAVSSEETNDFK) (SEQ ID NO: 34) at positions 58 to 70 of the open reading frame. This sequence shows a high level of homology among mammal species. Secondary structure prediction makes this sequence appropriate to solvent exposure and this sequence was shown to be phosphorylated at its serine residues. This latter characteristic is thought to affect binding to bone matrix (11).

Human Bone SialoProtein II (hBSP2) is a protein synthesized by osteoblasts that shows major similarities to a group of bone and teeth mineral matrix phosphor-glycoproteins, proteins known to naturally bind to bone matrix. Of particular importance, hBSP2presents at its amino-terminus a sequence of 18 amino acid residues at positions 62 to 79 of the open reading frame (GSSDSSEENGDDSSEEEE) (SEQ ID NO: 35) similar to acidic peptides found in dentin phosphorin and MEPE, and thought to promote binding to bone matrix (8).

Human Insulin-like Growth Factor binding protein-5 (hIGFBP5) is synthesized by osteoblasts. This protein, similarly to proteins of the IGFBP family, is thought to regulate osteoblast function in the bone remodeling process. Of particular importance, hIGFBP5 presents a sequence of 18 amino acid residues at positions 221 to 238 of the open reading frame (RKGFYKRKQCKPSRGRKR) (SEQ ID NO: 36) that was shown to bind tightly to hydroxyapatite (12).

*Staphylococcus aureus* collagen adhesin (M81736) is a protein expressed at the surface of *S. aureus* that promotes bacteria binding to collagen matrix of mammalian bone and cartilageneous tissues. Such a binding was reported to be instrumental in the development of pathogenesis such as osteomyelitis and infectious arthritis. Of particular importance, the collagen binding domain (CBS) of this adhesin was reported to encompass 151 amino acid residues (G168 to N318) of the open reading frame of the protein (13, 14). The amino acid primary sequence being the following:

GTSSVFYYKTGDMLPEDTTHVRWFLNINNEKSYVSK (SEQ ID NO:37)

DITIKDQIQGGQQLDLSTLNINVTGTHSNYYSGQSA

ITDFEKAFPGSKITVDNTKNTIDVTIPQGYGSYNSF

SINYKTKITNEQQKEFVNNSQAWYQEHGKEEVNGKS

FNHTVHN.

Plasmids containing the acidic peptide sequences derived from hMEPE, hStatherin, hMGP, hOPN, hBSP2, hIGFBP5 and CBS following GST in frame were constructed to determine whether they could promote bone targeting of a recombinant protein. Recombinant DNA technology as described in Example 1 was used to generate plasmids for hMEPE, hStatherin, hMGP, hOPN, hBSP2 and hIGFBP5 derived peptides. The oligonucleotide pairs identified in Table 1 for each of these peptides were mixed to obtain the corresponding GST-acidic peptide fusion protein. This procedure generated duplex oligonucleotides coding for these acidic peptides and having extremities compatible with cloning in the pGEX3T-4 (Pharmacia biotechnology) plasmid pre digested with restriction endonucleases BamHI and NotI.

A CBS-containing plasmid was constructed as follows. A synthetic gene corresponding to the CBS sequence was obtained from Bio S&T (Montreal) and inserted in plasmid pLIV Select. Oligonucleotides of SEQ ID NO: 27 and 28 were used as primers in PCR reactions with plasmid pLIV Select containing the CBS gene to amplify the CBS specific sequences. pGEX-4T-3 vectors were transformed into AP401 protease minus *E. coli* bacteria strain (Ion::mini tetR ara-Δlac-pro nalA argEam rifR thiI [F'pro AB lacIq Z M15]).

Protein production and purification, and pharmacodistribution of the iodinated fusion protein were performed as described in Example 1.

None of these GST-acidic peptides was shown to bind to bones (result not shown).

The fact that the peptide derived from statherin, a peptide shown to successfully deliver a small portion of osteopontin to bone, could not successfully deliver the GST protein to bone shows that it is not predictable whether a specific acidic peptide known to effectively deliver a small peptide to bone will also be effective in delivering a protein to bone.

EXAMPLE 3

$D_{10}$ Increases sPHEX's Ability to Correct Alkaline Phosphatase Levels in Mice PHEX is a metallopeptidase that is widely believed to control the level of bone peptide factors involved in the regulation of mineralization and kidney phosphate homeostasis. PHEX is expressed at the surface of osteoblasts and osteocytes in contact with or imbedded in the bone matrix. This example provides data on the design, production and purification of an extended form of sPHEX containing at its N-terminus a sequence of 10 aspartic acid residues designed to anchor itself to the bone matrix.

$D_{10}$sPHEX Expression Vector

A BspEl endonuclease restriction site was inserted by site directed mutagenesis (QuickChange, Stratagene) into the pCDNA3-RSV-sPHEX-NEO vector (Boileau G. et al., Biochem. J. (2001) 355, 707-13) using the following oligonucleotide primers:

(SEQ ID NO:38)
5'-CAGTCAAGGTCTCTTA<u>TCCGGA</u>AGTCTCCAAGCTAAACAGG-3'
and (SEQ ID NO:39)
5'-CTGTTTAGCTTGGAGACT<u>TCCGGA</u>TAAGAGACCTTGACTGG-3'

Figure 3:
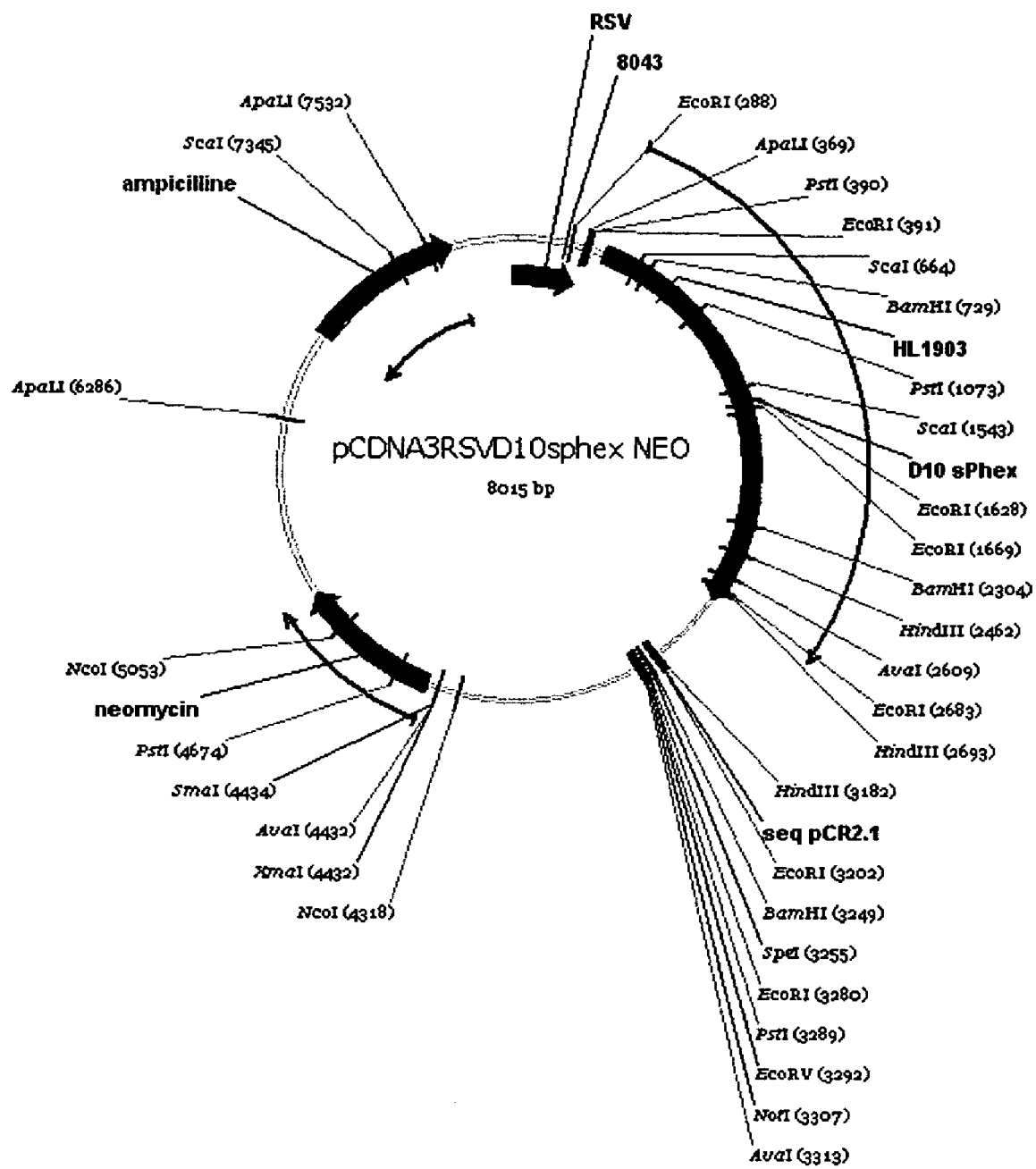
FIG. 3 provides a schematic representation of the plasmid pCDNA3-RSV-$D_{10}$sPHEX-NEO vector.

The hexamer BspEl sequence (underlined) was inserted in frame with and upstream of the sPHEX DNA sequence. This construct encodes a recombinant protein which is cleavable between the leucine and serine at positions 41 and 42, respectively in FIG. 8. It is constituted therefore of two exogenous amino acids, followed downstream by a deca-aspartate, which is in turn followed by two additional exogenous amino acids. These 4 exogenous amino acids derive from the cloning strategy used to produce the conjugate. These exogenous amino acids were shown not to defeat the enzymatic activity of the conjugate (See FIG. 12 showing the specific activity of this construct) but may be dispensed with. Downstream of these exogenous amino acids is an ectodomain fragment of the native PHEX starting therefore with the serine at position 46 of the sequence presented in FIG. 10. The modified pCDNA3-RSV-NEO vector was cleaved with BspEl and then digested with alkaline phosphatase to remove the 5' phosphate moieties. An oligonucleotide duplex coding for deca-aspartate: [5'-CCGGAGATGACGATGACGATGACGAT-GACGATGACT-3' (SEQ ID NO: 29) and 3'-TCTACTGCTACTGCTACTGCTACTGC-TACTGAGGCC-5' (SEQ ID NO: 30)] was first phosphorylated on its 5' ends with T4 polynucleotide kinase and ligated to the BspEl digested vector. This yielded the pCDNA3-RSV-$D_{10}$sPHEX-NEO vector (FIG. 3). This vector comprised the sequence presented in FIG. 7 which encodes the recombinant cleavable PHEX having the amino acid sequence presented in FIG. 8.

Expression of Recombinant $D_{10}$sPHEX

To induce the stable expression of the $D_{10}$sPHEX protein, the pCDNA3-RSV-$D_{10}$sPHEX-NEO vector was transfected in LLC-PK1 cells (Porcine Kidney cells; ATCC No. CRL-1392) using the Lipofectamine-Plus™ liposome transfection kit (Invitrogen). Transfected cells were selected by adding 400 µg/ml G-418 (Life Technologies) to the medium. Clones of G-418 resistant cells were screened for $D_{10}$sPHEX expression using the PHEX fluorescent enzymatic assay [Campos M. et al. Biochem. J. (2003) 373, 271-9]. The apparent molecular weight of the protein recovered in the spent medium was estimated by immunobloting using a monoclonal antibody raised against a recombinant human PHEX fragment (K121-E294) as described previously (Ruchon A F et al. J. Bone Miner. Res. (2000) 15, 1440-1450). A G-418 resistant clone expressing 1 to 2 mg of D10sPHEX per litre was used for protein production. Cells were seeded in Cellstack-10™ (Corning) at a density of $7 \times 10^7$ in 1.75 litres of media (199 media, 6% FBS, 1 mM NaPyruvate, Penicillin $1 \times 10^5$ U/litre, Streptomycin 100 mg/litre and 1% G-418. $D_{10}$sPHEX expression was increased by incubating the cells in 1.75 litre of DMEM+10 mM sodium butyrate for four days at 37° C. and 5% $CO_2$ prior to harvest of the spent medium.

Purification and Characterization

Figure 5:
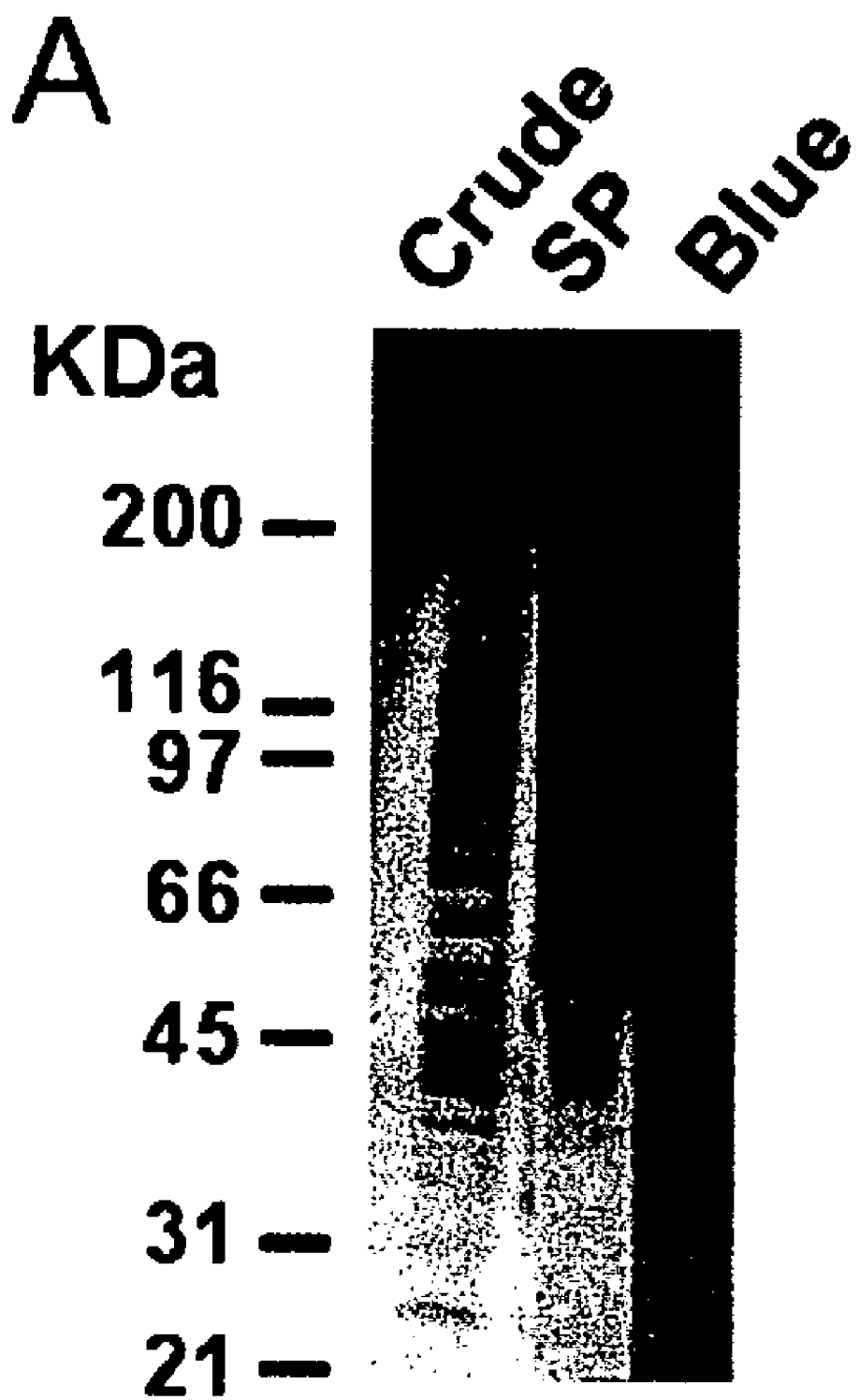
FIG. 5 presents a Sypro-ruby™ stained SDS-PAGE analysis of the different fractions collected throughout $D_{10}$sPHEX purification procedure.

Cell supernatant was centrifuged at 500×g for 5 minutes at 4° C. and filtered on fiberglass (Fisher, APFC09050) and concentrated 10 to 40 times using an Ultrasette™ 30 tangential flow filtration device (Pall Canada). The pH of the solution was brought to 5.6 with 1 M acetic acid before an overnight dialysis at 4° C. against 50 mM sodium acetate, 100 mM NaCl pH 5.6 (SP-buffer). The dialyzed supernatant was loaded, at a flow rate of 4 ml/min, on a 20 ml SulfoPropyl-Sepharose cation-exchange column (Amersham Pharmacia Biotech) previously equilibrated with SP-buffer. The column was washed with the same buffer at the same flow rate until 280 nm absorbance baseline was reached. Most of the contaminant proteins were then eluted with a 226 mM NaCl step in the SP buffer. D10sPHEX was then eluted with a 280 mM NaCl step (FIG. 4A). Fractions were analyzed by SDS-PAGE and with the PHEX enzymatic activity assay. Fractions containing sPHEX were pooled and extensively dialyzed against 20 mM MOPS pH 7, 250 mM NaCl prior to loading on a 5 ml Blue-Sepharose™ HP (Amersham Pharmacia) column at 5 ml/min. The column was rinsed, at the same flow rate with the same buffer and most of the D10sPHEX protein was recovered by increasing the NaCl concentration stepwise to 350 mM (FIG. 4B). Purity of the final fraction was greater than 95%. Alternatively, the Blue-Sepharose™ could be replaced by Heparin-Sepharose™ (Amersham Pharmacia) on which D10sPHEX binds tightly over a range of pH (5 to 8). D10sPHEX was eluted by using NaCl gradient. Purity was determined to be above 90%. D10sPHEX was concentrated and dialyzed against 1 mM sodium PO4 pH 7.4, 150 mM NaCl using Centriprep-50™ cartridges. Dialyzed sample was filtered in a sterile environment on 0.22 μm membrane. Purified D10sPHEX was shown to remain stable over months at 4° C. Protein concentrations were determined using the Bradford method (DC protein assay kit; Biorad) with bovine serum albumin (BSA) as a standard. Protein purity was assed by Sypro-Ruby™ (Molecular Probes) staining of proteins resolved on SDS-PAGE 4-12% (FIG. 5). D10sPHEX enzymatic activity was determined using the fluorigenic substrate.

Effect of sPHEX and $D_{10}$-sPHEX Injections on Circulating Levels of Alkaline phosphatase in HYP Mice The X-linked Hyp mice harbors a large deletion in 3' region of the PHEX gene and is the murine homologue of human X-linked hypophosphatemia (XLH). These mice therefore represent a useful model to study the pathophysiology of XLH as well as a to test the efficacy of therapeutic agents in preclinical studies.

The potential therapeutic effect of $D_{10}$sPHEX and sPHEX was thus investigated with bolus intravenous injection to Hyp/Y mice over a 2 week period.

$D_{10}$sPHEX and sPHEX were dialyzed against vehicle and the solutions were filtered through 0.22 μm low binding protein filter. The solutions were aliquoted and re-assayed for enzymatic activity and concentration by fluorogenic enzymatic assay and Bradford method, respectively.

Each mouse was anesthetized with vaporized Isoflurane (2%) and $D_{10}$sPHEX, or sPHEX were injected as an intravenous bolus through the subclavian vein. The dose was 5 mg/kg of body weight for each group. The animals were treated once daily for 14 consecutive days. Blood samples (0.1-0.2 ml) were collected via the subclavian vein under anesthesia on study days −3 and +15 (before necropsy, 24 hours after last injection). Total Alkaline phosphatase (ALP) levels were assayed in diluted serum (30 μl of serum sample with 90 μl of 0.9% saline USP). Although, appropriate dosages for human patients are not proportional to those used in mice, these dosages are predictive of the dosages ranges that could be suitable in humans using published tables.

Figure 6:
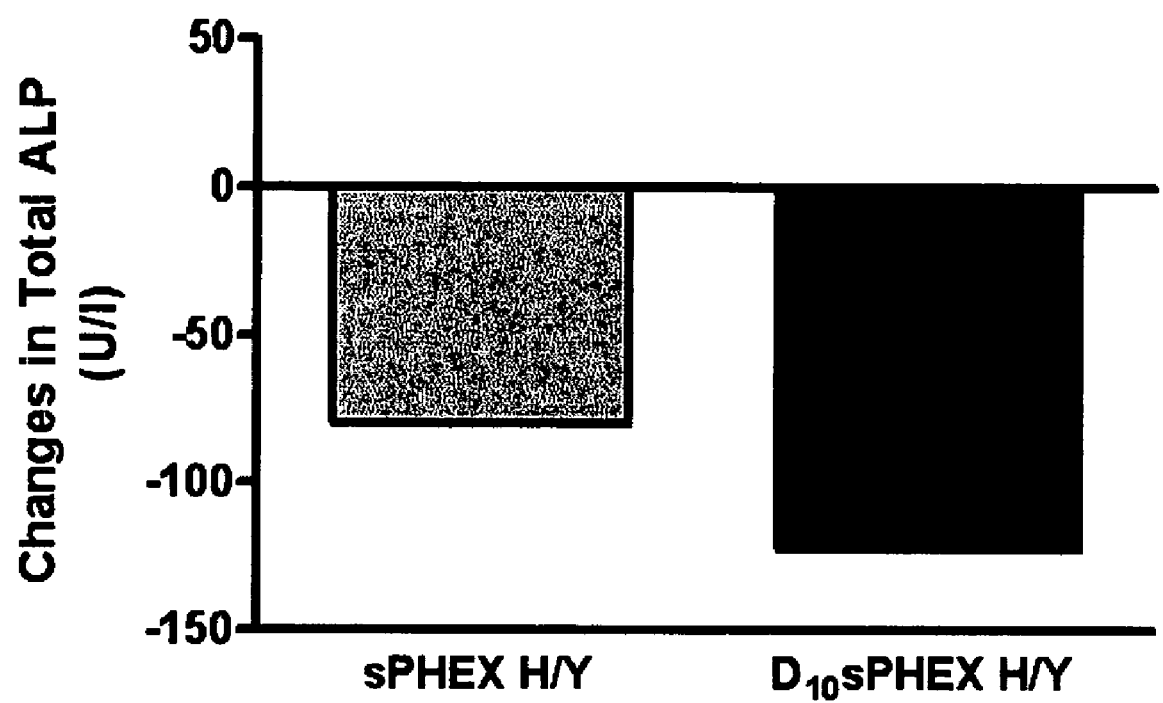
FIG. 6 shows the variation in serum alkaline phosphatase levels (ALP) observed in Hyp mice injected daily with i.v. doses of sPHEX and $D_{10}$-sPHEX for 14 days. U/l values represent the decrease observed between day-3 (corresponding in the graphic to 0 U/l) and day 15. of the injection regimen and are the mean of measures made on 6 animals.

As seen in FIG. 6 the $D_{10}$-extended form of sPHEX induced a larger decrease in alkaline phosphatase levels than the normal sPHEX form.

EXAMPLE 4

$D_{10}$ Fusion to Recombinant GST Increases its Binding to the Mineral Phase of Bone in Vitro Fluorescein Labelling of Purified Proteins Recombinant purified proteins were labelled with fluorescein-isothiocyanate (FITC, Molecular Probes F143). Reaction was carried out by adding proteins to 10 mM sodium phosphate, 50 mM NaCl buffer pH 7 at a final protein concentration of 1 mg/ml. Labelling reaction was started by adding FITC dissolved in DMSO at a concentration of 20 mg/ml to reach 20:1 molar ratio with respect to the protein concentration. The mixture was left to react at room temperature for an hour. Labelled protein was separated from the free fluorescein on a PD-10™ column (Pharmacia) prior to dialysis in the binding buffer (1 mM sodium phosphate 150 mM NaCl, pH 7.4).

Preparation of the Mineral Phase of Bones

Long bones were dissected from a rat and crushed to powder in a liquid nitrogen cooled mortar. The powder was either kept at −80° C. or directly used. An aliquot of the powder (300 mg) was washed 3 times with 8 ml of PBS and 8 ml of 1 M HCl were added. The mixture was kept in suspension on a rotating mixer for 1 hour at room temperature. The insoluble fraction was spun down and the clear acidic supernatant collected. This acidic solution was stable at room temperature for at least two weeks.

Binding Reaction

Aliquots of 20 μl of the acidic bone extract were mixed with 2 μl of 10 M NaOH and the precipitate was pelleted at 10,000×g for 3 minutes at room temperature. The pellet was rinsed twice by resuspending in 100 μl of binding buffer. The bone extract was then mixed with 100 μl of a solution containing 5 to 45 μg of fluorescein-labelled protein in the binding buffer to which phosphate was added to reach a final concentration of 80 mM. The samples were incubated for 30 minutes at room temperature on the rotating wheel to keep the mineral phase in suspension. The samples were then centrifuged for 3 minutes at room temperature. The pellet containing the bound protein was dissolved in 200 μl of 0.5 M EDTA pH 8. To estimate the amount of free protein present, 100 μl of 0.5 M EDTA pH 8 was added to the supernatant. Fluorescence of the different samples was measured on a 96 wells plate reader set at 494 nm for excitation and 516 nm for emission.

Results

Figure 9:
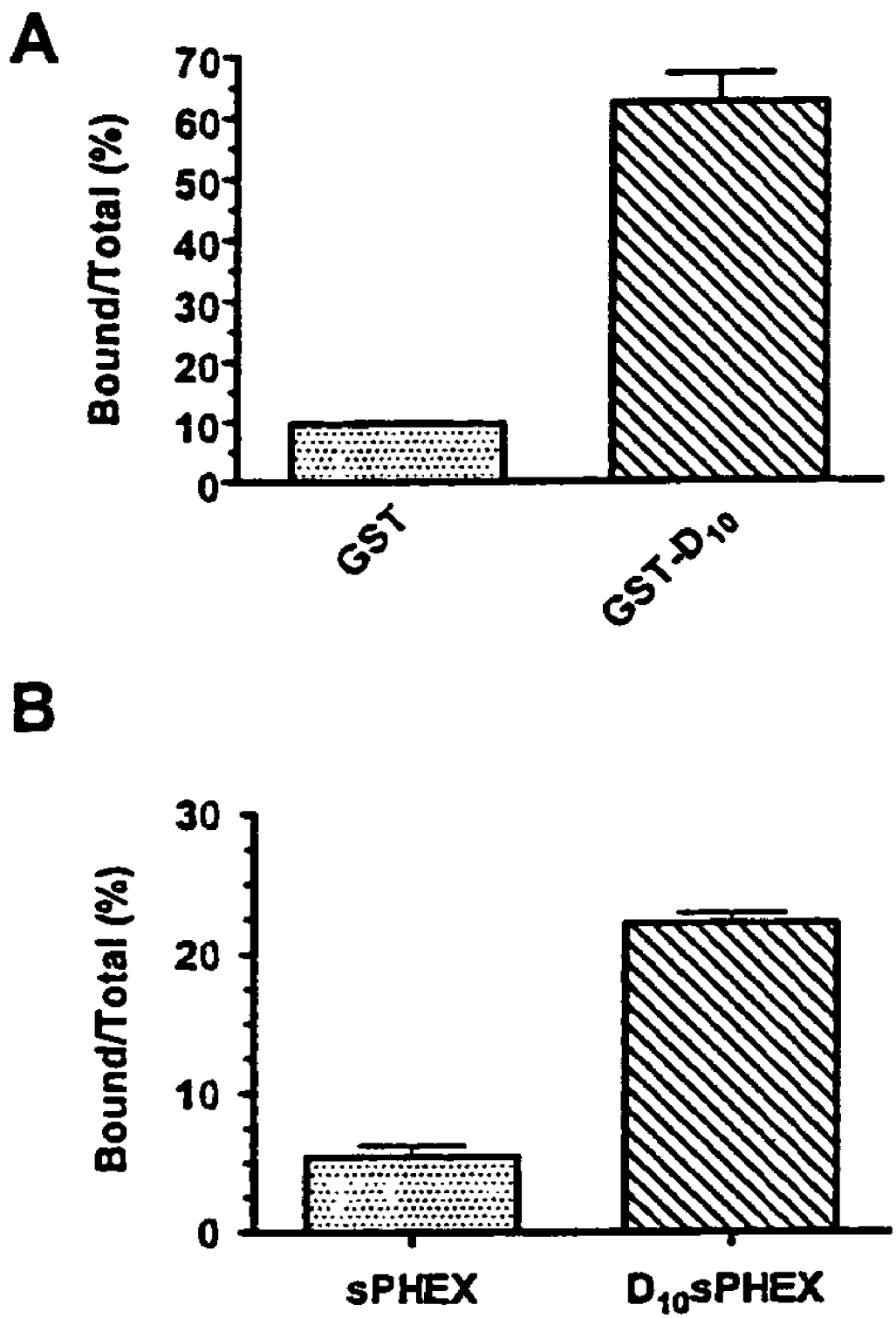
FIG. 9 compares the binding to the mineral phase of bone of proteins (A. GST B. sPHEX) with that of their decaaspartate fused counterparts.

Samples containing 50 μg of fluorescein-labelled GST and GST-$D_{10}$ were used in the binding assay described above. FIG. 9A shows that fusion of the $D_{10}$ sequence to GST caused a 6-fold increase in binding to the mineral phase of bone.

EXAMPLE 5

$D_{10}$ Fusion to sPHEX Increases its Binding to Bone

Using a procedure analogous to that described in Example 4 above, samples containing 50 μg of fluorescein-labelled sPHEX and $D_{10}$sPHEX were used in a binding assay. FIG. 9B shows that fusion of the $D_{10}$ sequence to sPHEX caused a 4.3 increase in binding to the mineral phase of bone.

In contrast, $D_6$-sPHEX was constructed and tested after in vivo injection in animals (as described in Example 1 above) and did not promote binding of recombinant proteins to bone (Data not shown).

EXAMPLE 6

$D_{10}$ Fusion to a Soluble Form of Alkaline phosphatase Increases its Targeting to the Mineral Phase of Bone Construction of Expression Vectors Encoding Human Recombinant Soluble Phosphatase Alkaline, sALP and sALP-$D_{10}$ The human full length cDNA encoding tissue non-specific alkaline phosphatase (ALP) was obtained from bone marrow polyA RNA (Clonetech) by RT-PCR. Briefly, 20 ng of polyA was reverse transcribed with SuperscriptII™ and an oligo$_{dT12-18}$ using the First Strand Synthesis System (Invitrogen). An aliquot representing 1/20$^{th}$ of the RT step was used directly in a PCR reaction with ALP specific oligos (forward 5'-gataaagcaggtcttggggtgcacc-3' (SEQ ID NO: 40); reverse 5'-gttggcatctgtcacgggcttgtgg-3' (SEQ ID NO: 41)) and the Expand High Fidelity Enzyme Kit™ (Roche). The resulting ALP specific product (1644 bp) was separated on and purified from an agarose gel (1%) using the Qiaquick Gel Extraction Kit™ (QIAGEN). The ALP cDNA was then ligated into the pCR4-blunt-TOPO™ vector (Invitrogen), transformed into Top10™ bacteria (Invitrogen), and a positive clone identified by colony PCR. The identity of the cDNA was verified by automated DNA sequencing.

Secreted forms of ALP (sALP) having the GPI anchor signal removed were constructed by PCR using Expand High Fidelity Enzyme Kit™. They comprised residues 1-502 followed by either a stop codon (sALP) or a deca aspartate targeting motif and a stop codon (sALP-D10). In both cases the forward primer (5'-tggatccaccatgatttcaccattcttagtac-3' (SEQ ID NO: 42)) covered the initiator methionine (underlined) and included a BamHI site (italicized). The reverse primers (sALP: 5'-ttctagactacgagctggcaggagcacagtggccg-3' (SEQ ID NO: 43); sALP-D10 5'-ttctagactagtcgtcatcatcgtcat-catcgtcgtcatccgagctggcaggagcacagtggccg-3' (SEQ ID NO: 44)) contained a stop codon (underlined) and an XbaI site (italicized). The PCR products were digested with BamHI and XbaI and cloned into the pCDNA3.1-RSV that had been pre-digested with the same enzymes. Plasmid DNA were sequenced.

ALP Fluorescent Enzymatic Assay

Enzymatic activity of sALP and sALP-$D_{10}$ was assayed using 4-methylumbelliferyl phosphate (MUP, Molecular Probes, M8425) as a fluorigenic substrate according to Gee K R et al. (Anal. Biochem. 273, 41-48 (1999)) Typically, the assay was carried out at 37° C. in 96-well plates in a final volume of 200 µl with 10 µM of MUP. Readings were recorded using a Spectramax Gemini™ (Molecular Devices) plate reader every minute for 30 minutes at 450 nm upon excitation at 360 nm. Emission wavelength cut-off was set at 435 nm. ALP initial speed rate was estimated by linear regression fitting (with $r^2$ equal or greater than 0.98).

Expression of Recombinant sALP and sALP-$D_{10}$ Proteins

In order to determine whether the recombinant sALP and sALP-$D_{10}$ proteins were secreted, each construct (pCDNA3-RSV-sALP-NEO and pCDNA3-RSV-sALP-$D_{10}$-NEO) was transiently transfected in HEK-293S cells (Human Embryonic Kidney cells; ATCC No. CRL-1392) using the Lipofectamine-Plus liposome transfection kit™ (Invitrogen). HEK-293S cells were also mock-transfected as a negative control. The day after transfection, cells were incubated for 24 h in serum-free DMEM. The conditioned media were collected and centrifuged at 14000 RPM for 5 min at 4° C. to remove dead cells and debris. The supernatants were assayed for sALP or sALP-$D_{10}$ enzymatic activity and expression using the ALP fluorescent enzymatic assay and Western blotting respectively. For Western blotting, the spent media were precipitated for 1 h on ice with trichloroacetic acid (final concentration 10% (v/v)). The precipitated proteins were spun down at 14000 RPM for 20 min at 4° C., washed once with chilled acetone, dried, and resuspended in 60 µl 1× Laemmli sample buffer with DTT and boiled for 5 min.

To evaluate the intracellular content of sALP and sALP-$D_{10}$ the cells were washed 3 times with PBS and lysed with 200 µl Tris-HCl 50 mM (pH 8) containing 150 mM NaCl and 1% NP-40 on ice for 20 min. The lysates were spun down and the supernatant was assayed for sALP or sALP-$D_{10}$ enzymatic activity and expression using the ALP fluorescent enzymatic assay and Western blotting, respectively. For Western blotting, 50 µl aliquots were mixed with 10 µl 6× Laemmli sample buffer with DTT and boiled for 5 min.

Samples were loaded on a Novex precast™ 4-12% Tris-Glycine polyacrylamide gel (Invitrogen) and transferred onto 0.45µm nitrocellulose (Protran, Schleicher&Schuell, Keene, N H) with Tris-glycine containing 10% methanol. The membrane was stained with Ponceau red and blocked for 1 h at room temperature with PBS containing 0.05% Tween 20™ (PBST) and 5% dried milk. The membrane was then sequentially incubated at room temperature with the anti-hBAP antibody (mAb 4B-78, Developmental Studies Hybridoma Bank) (1:1000 in PBST with 5% dried milk) and a rabbit anti-mouse IgG coupled to horseradish peroxidase (Sigma) (1:12000 in PBST with 5% dried milk). The signal was developed with the Western Lightning Chemiluminescence Reagent Plus™ (PerkinElmer).

Figure 13:
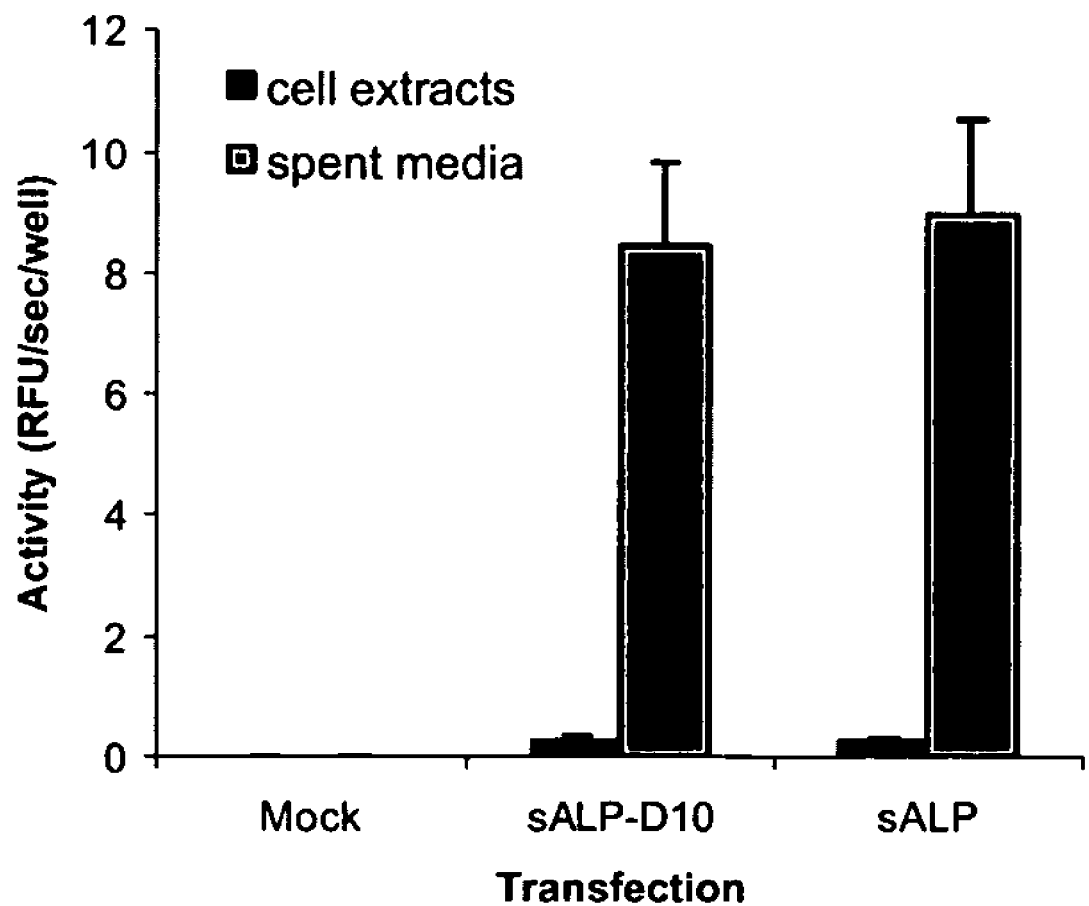
FIG. 13 graphically illustrates through fluorimetric measurement of the alkaline phosphatase activity in the soluble cell extract and spent medium of HEK293 transiently transfected with expression vectors encoding sALP-$D_{10}$ and sALP.
Figure 14:
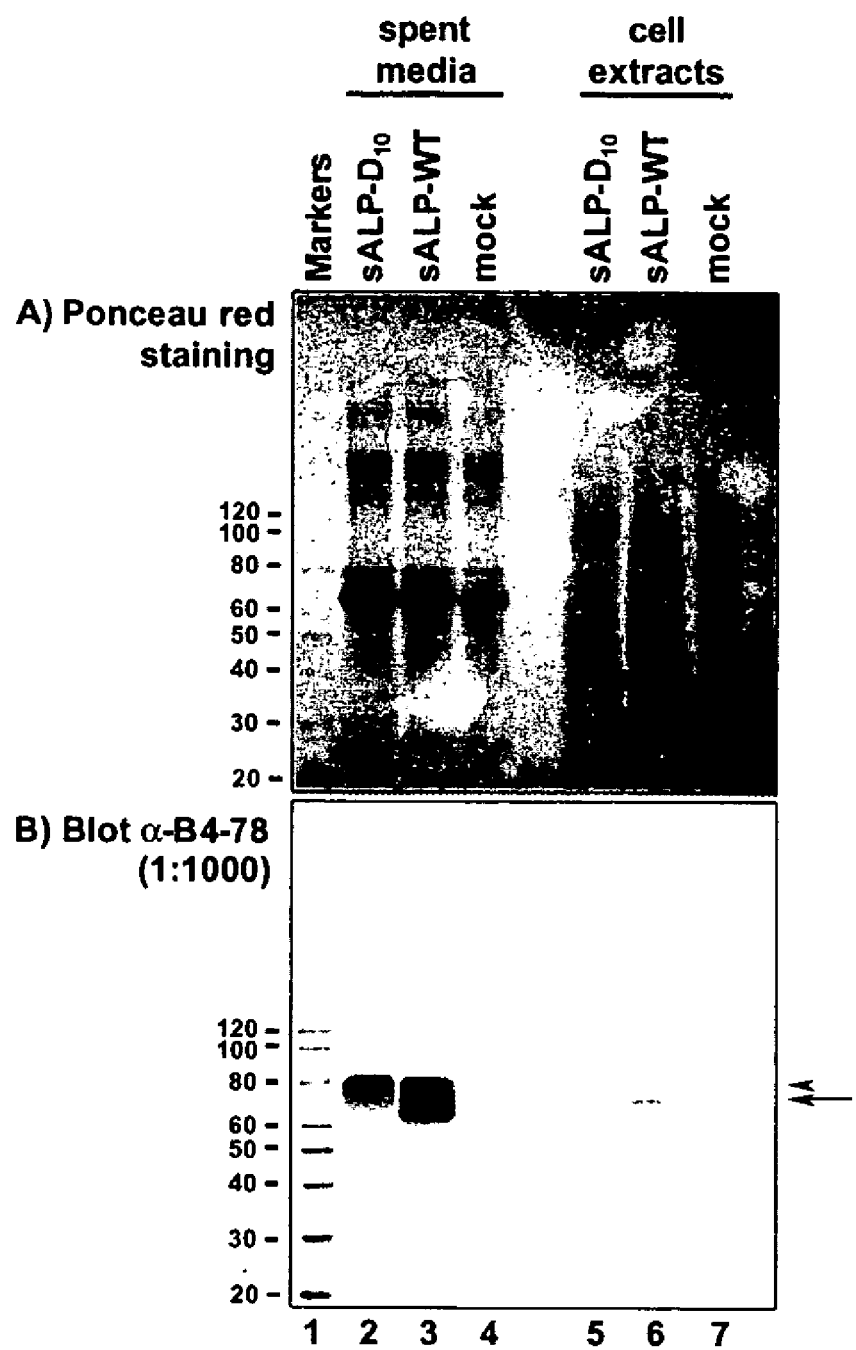
FIG. 14 graphically illustrates the detection of sALP and sALP-$D_{10}$ by Western blotting with the specific B4-78 antibody in the spent media and cell extract of HEK-293 after transient transfection. (Panel A: Ponceau red staining; Panel B: Blot a-B4-78). Shown on the left are the sizes of the molecular weight markers.
Figure 15:
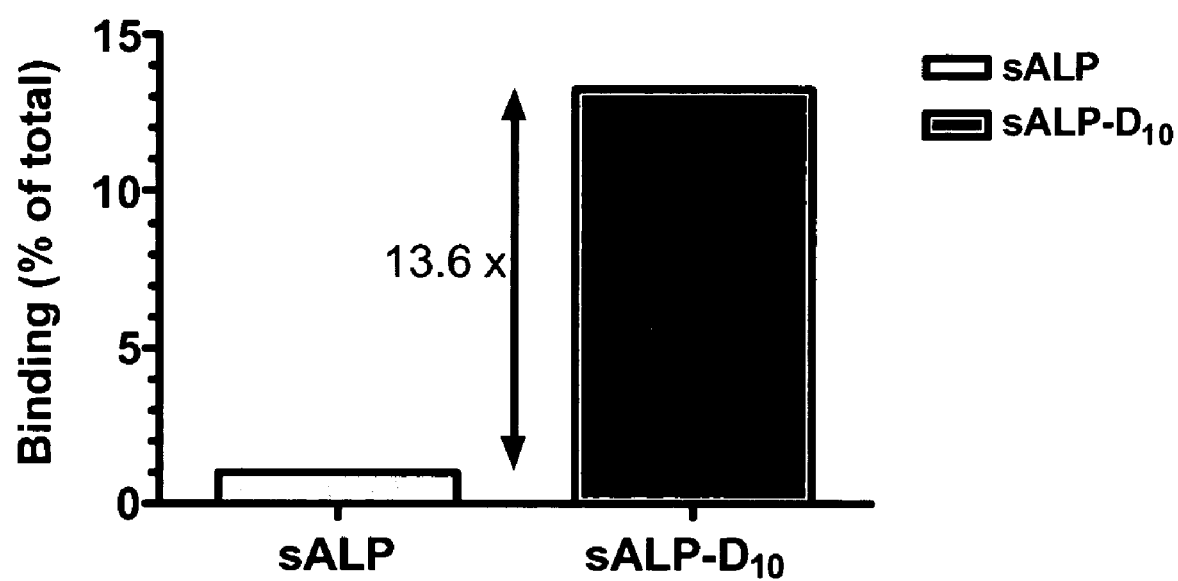
FIG. 15 graphically shows the binding to bone mineral phase of a deca-aspartate fused to secreted alkaline phosphatase.
Figure 18:
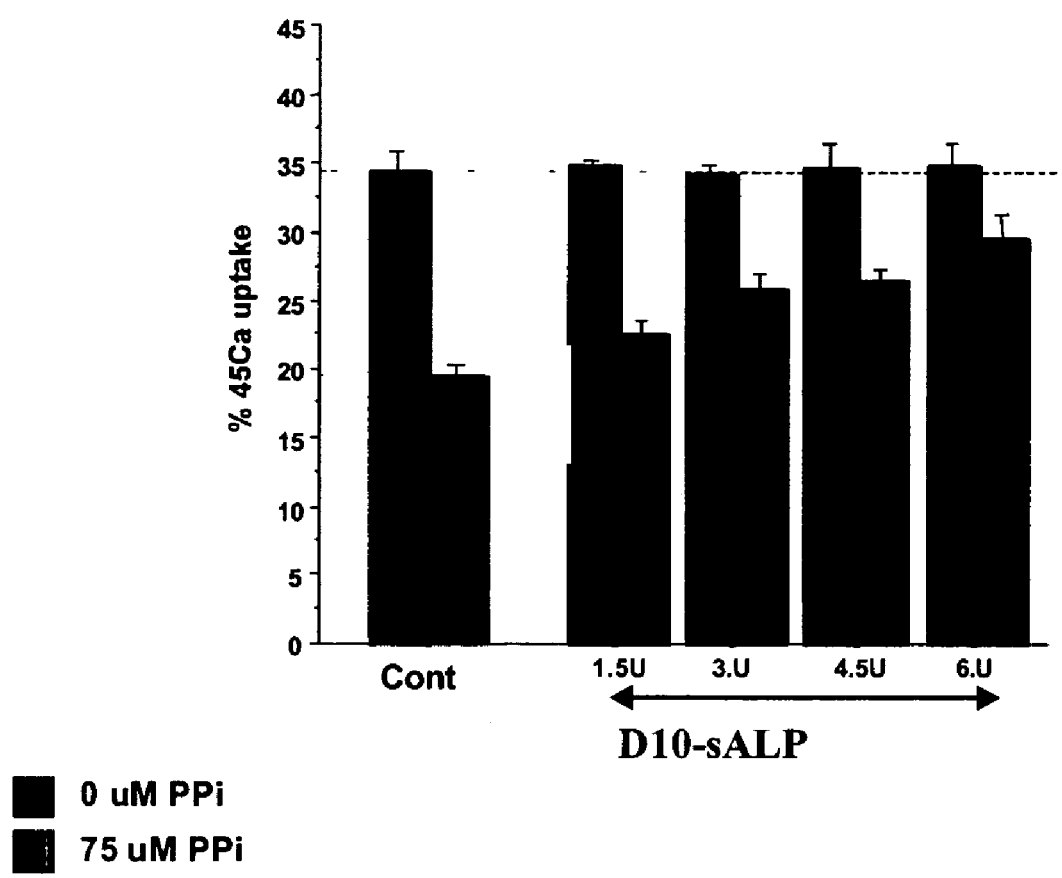
FIG. 18 graphically shows the effect of sALP-D10 on PPi-mediated mineralization inhibition.

The ALP enzymatic activity measured in the conditioned media of HEK293 after transient transfection was very high and of similar magnitude for pCDNA3-RSV-sALP-NEO (sALP) and pCDNA3-RSV-sALP-$D_{10}$-NEO (sALP-$D_{10}$) (FIG. 13). This activity was specific to the plasmid DNA transfected as it was undetectable in mock-transfected cells (mock). The relative activity measured in the media was 35-times greater than that measured in the cell extracts thus attesting to the secretory nature of sALP and sALP-$D_{10}$. Accordingly, for both sALP and sALP-$D_{10}$, immunoblotting using a monoclonal antibody raised against recombinant tissue nonspecific human alkaline phosphatase (mAb 4B-78, Developmental Studies Hybridoma Bank) revealed a much stronger signal in the conditioned media than in the cell extracts (FIG. 14B, compare lanes 2, 3 vs. 5, 6). No signal was visualized in the mock-transfected samples (FIG. 14B, lanes 4 and 7). The signal appearing in the mock-transfected cells consists of BSA trace. The apparent molecular weight of the protein detected was estimated to be 70 kDa in the cell extracts (arrow) and slightly higher in the conditioned media (arrowhead). Ponceau red staining of the membrane was performed to monitor the uniform loading of samples (FIG. 14A).

Generation of HEK293 Cells Constitutively Secreting sALP and sALP-$D_{10}$

To induce the stable expression of the sALP and sALP-$D_{10}$ proteins, the pCDNA3-RSV-sALP-NEO and pCDNA3-RSV-sALP-$D_{10}$-NEO vectors was transfected separately in HEK-293S cells using the Lipofectamine-Plus liposome transfection kit™ (Invitrogen). Transfected cells were selected by adding 800 µg/ml G418 (Life Technologies) to the medium. For each transfection a pool of G-418 resistant cells were analyzed for sALP or sALP-$D_{10}$ expression in the spent culture media using the ALP fluorescent enzymatic assay. The conditioned media collected from the stable cell lines were used for the binding assay study on the bone mineral.

Binding to Reconstituted Mineral Phase of Bone

Aliquots of 20 µl of the acidic bone extract were mixed with 2 µl of 10 M NaOH and the precipitate was pelleted at 10,000×g for 3 minutes at room temperature. The pellet was rinsed twice in 100 µl of buffer (1 mM sodium phosphate pH 7.4+150 mM NaCl). The resultant mineral phase of bone (equivalent to 0.37 mg of dried powder) was then mixed with 100 µl of a solution containing sALP or sALP-$D_{10}$ proteins in the binding buffer (80 mM sodium phosphate pH 7.4+150 mM NaCl). The samples were incubated for 30 minutes at room temperature on the rotating wheel to keep the mineral phase in suspension. The samples were then centrifuged for 3 minutes at room temperature. The pellet containing the bound protein was mixed with 180 µl of the ALP enzymatic assay buffer containing 0.1% BSA and the reaction initiated by adding 20 µl of 100 µM MUP. To allow for more homogeneous assay, conditions the 96 wells plate was shaken for 10 seconds every minute for the duration of the assay.

Enzymatic activity retained on reconstituted mineral bone phase was compared to the equivalent enzymatic activity added in the binding assay. Values of 0.98% and 13.3% of total protein activity bound to the bone mineral phase were calculated for sALP and sALP-$D_{10}$ respectively. A binding difference of more than 13 times in favour of sALP-$D_{10}$ suggests that the C-terminal fused deca-aspartate sequence directly targets sALP to the mineral phase of bone. Furthermore, the fact that it was possible to measure directly ALP activity bound to the mineral phase of bone indicates that the enzyme is bound in a catalytically competent form to hydroxyapatite crystals.

Such fusion protein can be targeted directly to bones where the accumulation of PPi inhibits skeletal mineralization.

EXAMPLE 7

ALP-$D_{10}$ decreases inhibitory effect of pyrophosphate on bone mineralization UMR106 cells were grown to confluence. They were then cultured for a further 7 days in media containing 10 mM β-glycerophosphate to induce mineralization. Throughout this 7-day culture period, cells were treated with or without 75 µM pyrophosphate (PPi), a mineralization inhibitor and a alkaline phosphatase substrate. To assess the ability of alkaline phosphatase to rescue the PPi-induced mineralization inhibition, cells treated with or without PPi were cultured with varying concentrations of semi-purified sALP-$D_{10}$ produced from HEK293, human embryonic kidney cells. Mineralization was assessed by $^{45}$Ca uptake. Parameters used for this experiment are presented in table 2 below.

TABLE 2

PARAMETERS USED IN ALP-$D_{10}$ ON PPi-INDUCED MINERALIZATION INHIBITION

| ALP | [ALP] (Units/well) | µl ALP/well | β-GP (mM) | PPi (µM) |
|---|---|---|---|---|
| — | 0 | 0 | 10 | 0 |
| — | 0 | 0 | 10 | 75 |
| sALP-$D_{10}$ | 1.5 | 0.5 | 10 | 0 |
| sALP-$D_{10}$ | 1.5 | 0.5 | 10 | 75 |
| sALP-$D_{10}$ | 3 | 1.0 | 10 | 0 |
| sALP-$D_{10}$ | 3 | 1.0 | 10 | 75 |
| sALP-$D_{10}$ | 4.5 | 1.5 | 10 | 0 |
| sALP-$D_{10}$ | 4.5 | 1.5 | 10 | 75 |
| sALP-$D_{10}$ | 6 | 2 | 10 | 0 |
| sALP-$D_{10}$ | 6 | 2 | 10 | 75 |

7-days of treatment with PPi resulted in a 43% decrease in mineralization. Co-treatment of cultures with sALP-$D_{10}$ resulted in a dose-responsive rescue of this mineralization inhibition. Treatment with 1.5 units sALP-$D_{10}$ resulted in a 30% decrease, 3 and 4.5 units a 24% decrease and 6 units resulted in a 15% decrease in mineralization, corresponding to a 65% rescue of PPi-induced mineralization inhibition.

These results show that the treatment of mineralizing osteoblast with sALP-$D_{10}$ dose-responsively rescues mineralization inhibition induced by PPi.

The above Examples shows that a poly-aspartate fusion to recombinant proteins increases their binding to the mineral phase of bone or to bone tissue and increases the ability of the protein to perform its biological activity as compared to when it is administered alone.

Although the present invention has been described hereinabove by way of preferred embodiments thereof, it can be modified, without departing from the spirit and nature of the subject invention as defined in the appended claims.

REFERENCE

1-Weinberg, J M (2003) An overview of infliximab, etanercept, efalizumab, and alefacept as biologic therapy for psoriasis. Clin Ther 25: 2487-2505.

2-Whyte M P, Valdes R Jr, Ryan L M, McAlister W H (1982) Infantile hypophosphatasia: enzyme replacement therapy by intravenous infusion of alkaline phosphatase-rich plasma from patients with Paget bone disease. J Pediatr 101: 379-386.

3-Whyte M P, Kurtzberg J, McAlister W H, Mumm S, Podgornik M N, Coburn S, Ryan L M, Miller C R, Gottesman G S, Smith A K, Douville J, Waters-Pick B, Armstrong R D, Martin P L (2003) Marrow cell transplantation for infantile hypophosphatasia. J Bone Miner Res 18: 624-636.

4-Fujisaki J, Tokunaga Y, Takahashi T, Shimojo F, Kimura S, Hata T (1997) Osteotropic drug delivery system (ODDS) based on biphosphonic prodrugs. IV: Effects of osteotropic estradiol on bone mineral density and uterine weight in ovariectomized rats. J Drug Targeting 5: 129-138.

5-Uludag H, Gao T, Wohl G R, Kantoci D, Zemicke R F (2000) Bone affinity of a biphosphonate-conjugated protein in vivo. Biotechnol Prog 16: 1115-1118.

6-Sekido T, Sakura N, Higashi Y, Miya K, Nitta Y, Nomura M, Sawanishi H, Morito K, Masamune Y, Kasugai S, Yokogawa K, Miyamoto K-I (2001) Novel drug delivery system to bone using acidic oligopeptides: pharmacokinetic characteristics and pharmacological potential. J Drug Targeting 9: 111-121.

7-Hunter G K, Kyle C L, Goldberg H A (1994) Modulation of crystal formation by bone phosphoproteins: structural specificity of the osteopontin-mediated inhibition of hydroxyapatite formation. Biochem J 300: 723-728.

8-Rowe P S N, de Zoysa P A, Dong R, Wang H R, White K E, Econs M J, Oudet C L, (2000) MEPE, a new gene expressed in bone marrow and Tumors causing osteomalacia. Genomics 67: 54-68.

9-Gilbert M, Shaw W J, Long J R, Nelson K, Drobny G P, Giachelli C M, Stayton P S, (2000) Chimeric peptides statherin and osteopontin that bind hydroxyapatite and mediate cell adhesion. J Biol Chem 275: 16213-16218.

10-Young M F, Kerr J M, Ibaraki K, Heegaard A M, Robey P G (1992) Structure, expretion, and regulation of the mayor noncollagenous matrix Proteins of bones. Clin Orthop 281: 275-294.

11-Sqalih E, Ashkar S, Gerstenfeld F C, Glimcher M J, (1997) Identification of the phosphorylated sites of metabollicaly 32P-labeled osteopontin from cultured chicken osteoblast. J Biol Chem 272: 13966-13973.

12-Campbell P G, Andress D L (1997) Insulin-like growth factor (IGF)-binding protein-5-(201-218) region regulates hydroxyapatite and IGF-I binding. Am J Physiol 273: E1005-E1013.

13-Patti J M, House-Pompeo K, Boles J O, Garza N, Gurusiddappa S, Hook M (1995) Critical residues in the ligand-binding site of the Sthaphylococcus aureus collagen-binding adhesion (MSCRAMM). J Biol Chem 207: 12005-12011.

14-Symersky J, Patti J M, Carson M, House-Pompeo K, Teale M, Moore D, Jin L, Schneider A, DeLucas L J, Hook M, Narayana S V (1997) Structure of the collagen-binding domain from a Staphylococcus aureus adhesion. Nat Struct Biol 4: 833-838.

What is claimed is:

1. A bone delivery conjugate comprising the structure: Z-protein-Y-Dn-X,
   wherein X is absent or is an amino acid sequence of at least one amino acid;
   Y is absent or is an amino acid sequence of at least one amino acid;
   Z is absent or is an amino acid sequence of at least one amino acid;
   Dn is a poly aspartate wherein n=10 to 16; and
   wherein said protein is a secreted soluble form of an alkaline phosphatase (sALP) having an amino acid sequence encoded by the sequence as set forth in SEQ ID NO: 5.

2. A bone delivery composition comprising the bone delivery conjugate of claim 1, and a pharmaceutically acceptable carrier.

3. The bone delivery conjugate of claim 1, wherein Y is an amino acid sequence of at least one amino acid and X and Z are absent.

4. The bone delivery conjugate of claim 3, wherein n is 10.

5. The bone delivery conjugate of claim 1, wherein n is 10.

6. A method of delivering ALP to bone tissue of a mammal in need thereof comprising administering to said mammal an effective amount of a bone delivery conjugate comprising the structure: Z-protein-Y-Dn-X,
   wherein X is absent or is an amino acid sequence of at least one amino acid;
   Y is absent or is an amino acid sequence of at least one amino acid;
   Z is absent or is an amino acid sequence of at least one amino acid;
   Dn is a poly aspartate wherein n=10 to 16; and
   wherein said protein is a secreted soluble form of an alkaline phosphatase (sALP) having an amino acid sequence encoded by the sequence as set forth in SEQ ID NO: 5.

7. A method of treating a condition or disease related to a bone defect characterized by a lack of or an insufficient amount of functional alkaline phosphatase comprising administering to a mammal in need thereof a conjugate comprising the structure: Z-protein-Y-Dn-X,
   wherein X is absent or is an amino acid sequence of at least one amino acid;
   Y is absent or is an amino acid sequence of at least one amino acid;
   Z is absent or is an amino acid sequence of at least one amino acid;
   Dn is a poly aspartate wherein n=10 to 16; and
   wherein said protein is a secreted soluble form of an alkaline phosphatase (sALP) having an amino acid sequence encoded by the sequence as set forth in SEQ ID NO: 5; and
   and wherein the conjugate is in a pharmaceutically acceptable carrier.

8. The method of claim 7, wherein the condition or disease is hypophosphatasia.

* * * * *

UNITED STATES PATENT AND TRADEMARK OFFICE
CERTIFICATE OF CORRECTION

PATENT NO.         : 7,763,712 B2
APPLICATION NO.    : 11/111664
DATED              : July 27, 2010
INVENTOR(S)        : Crine et al.

Page 1 of 1

It is certified that error appears in the above-identified patent and that said Letters Patent is hereby corrected as shown below:

Title Page, under OTHER PUBLICATIONS, in Henthorn and Whyte,
  replace "38/12, 2501-2505 (1992)" with --38(12): 2501-2505 (1992)--.

Page 2, under OTHER PUBLICATIONS, in Spears et al., replace "Deoxyuridate" with
  --Deoxyuridylate--.

Column 10, Line 36, replace "day 15." with --day 15--.

Column 12, under TABLE 1-continued, Lines 22-24, after SEQ ID
  NO:26, replace "5′-GGCCGCACGCTTGCGGCCACGGAAGGTTTGCACTGCT
  TTCTCTTGTAGAATCCTTTGCGG-3′" with --5′-GGCCGCACGCTTGCGGCC
  ACGGGAAGGTTTGCACTGCTTTCTCTTGTAGAATCCTTTGCGG-3′--;

Under Table 1-continued, Line 31, before SEQ ID NO:29, insert --$D_{10}$--.

Column 16, Line 51, replace "immunobloting" with --immunoblotting--.

Column 17, Line 34, replace "assed" with --assessed--.

Column 21, Line 21, replace "assay, conditions the 96 wells plate" with --assay conditions,
  the 96 well plate--.

Column 23, Line 10, replace "expretion" with --expression--;
  Line 10, replace "mayor" with --major--;
  Line 11, replace "Proteins" with --proteins--;
  Line 13, replace "Sqalih" with --Salih--.

Column 60, Line 61, delete "and".

Signed and Sealed this
Third Day of July, 2012

David J. Kappos
*Director of the United States Patent and Trademark Office*